(12) United States Patent
Vander Meer et al.

(10) Patent No.: US 10,568,320 B2
(45) Date of Patent: Feb. 25, 2020

(54) BIOLOGICALLY-BASED CONTROL METHODS FOR INSECT PESTS

(71) Applicants: The United States of America, as represented by the Secretary of Agriculture, Washington, DC (US); Foresight Science & Technology, Inc., Hopkinton, MA (US)

(72) Inventors: Robert K. Vander Meer, Newberry, FL (US); Satya P. Chinta, Gainesville, FL (US)

(73) Assignees: The United States of America, as represented by the Secretary of Agriculture, Washington, DC (US); Foresight Science & Technology Inc., Hopkinton, MA (US)

(*) Notice: Subject to any disclaimer, the term of this patent is extended or adjusted under 35 U.S.C. 154(b) by 0 days.

(21) Appl. No.: 15/908,105

(22) Filed: Feb. 28, 2018

(65) Prior Publication Data
US 2018/0249708 A1    Sep. 6, 2018

Related U.S. Application Data

(60) Provisional application No. 62/465,503, filed on Mar. 1, 2017.

(51) Int. Cl.
*A01N 33/10* (2006.01)
*A01M 1/20* (2006.01)
*A01N 25/00* (2006.01)

(52) U.S. Cl.
CPC .......... *A01N 33/10* (2013.01); *A01M 1/2011* (2013.01); *A01N 25/006* (2013.01); *A01M 2200/011* (2013.01)

(58) Field of Classification Search
CPC .......... A01M 1/2011; A01M 2200/011; A01N 25/006; A01N 33/10
See application file for complete search history.

(56) References Cited

U.S. PATENT DOCUMENTS

| | | | |
|---|---|---|---|
| 4,678,775 A * | 7/1987 | Nathanson | A01N 33/04 514/183 |
| 9,950,994 B2 * | 4/2018 | Jones | C07C 235/74 |
| 2013/0289125 A1 * | 10/2013 | Jones | A01N 37/18 514/630 |
| 2018/0009740 A1 * | 1/2018 | Jones | C07C 235/08 |

* cited by examiner

*Primary Examiner* — Kara R McMillian
(74) *Attorney, Agent, or Firm* — John Fado; G. Byron Stover

(57) ABSTRACT

The present invention provides novel compositions and methods for using the insect neuromodulator tyramine and/or one or more derivatives thereof delivered to insect populations to control certain aspects of such populations. The amount of tyramine and/or one or more derivatives thereof delivered on a per insect basis is significantly greater than a naturally-occurring amount of tyramine normally found in insects and causes deleterious effects including mortality of certain insect life forms and disruption of the reproductive capacity of others in the population.

15 Claims, 22 Drawing Sheets

BIOLOGICALLY-BASED CONTROL METHODS FOR INSECT PESTS

CROSS REFERENCE TO RELATED APPLICATION

This application claims priority to U.S. Provisional Patent Application Ser. No. 62/465,503, filed Mar. 1, 2017, the content of which is incorporated herein by reference in its entirety.

FIELD OF THE INVENTION

The disclosed invention relates generally to compositions and methods for controlling pest social insect populations using naturally-occurring or synthetic biogenic amine compounds or derivatives thereof. More specifically, the invention relates to compositions and methods for exposing targeted ant colonies to such biogenic amines for the control and elimination of the colonies.

BACKGROUND OF THE INVENTION

Ants comprise 5% of the world's 100 worst invasive alien species and 28% of land invertebrates (see Lowe S., et al., (2000). 100 of the World's Worst Invasive Alien Species A selection from the Global Invasive Species Database. Published by The Invasive Species Specialist Group (ISSG) a specialist group of the Species Survival Commission (SSC) of the World Conservation Union (IUCN), 12 pp). It has been estimated that there are over twenty thousand ant species occupying every ecological niche as part of the structure of ecological communities (see Holldobler and Wilson, The Ants. Harvard University Press, Cambridge, 1990; Smith et al., Cold Spring Harb. Protoc. 4:1, 2009), and over 12,500 currently described (antbase.org, 15 Jan. 2010). However, some of the ant species, especially those moved through human activities to non-native locations, have become serious pests (see Lessard et al., Ecology 90:2664, 2009; Porter and Savignano, Ecology 71:2095, 1990). The Myrmicinae subfamily, for example, is the largest of the 21 extant subfamilies in the ants (Hymenoptera: Formicidae) (Bolton, Mem. Am. Entomol. Inst. 71:1, 2003). The Myrmicinae subfamily includes about 140 genera within the group, including species with a functional sting (such as, for example, ants in the genus *Solenopsis*, one of which is *S. invicta*, known as the "red imported fire ant," and *Myrmica rubra*, also known as the European fire ant or common red ant), and fungus-growing ants (of the tribe Attini, e.g., leafcutter ants (genus *Atta* and genus *Acromyrmex*). Collectively and individually, these and other ant species are considered pests in commercial, agricultural, and residential settings, causing significant damage and injury to crops and livestock and a host of other economic sectors, as well as potential medical issues (e.g., humans and animals can develop hypersensitivity to fire ant venom that may result in anaphylactic shock and death).

Global commerce ensures that these invasive pest species, including social insects such as various ant species (e.g., imported/invasive fire ants) will be distributed to compatible habitats throughout the world. For example, it is estimated that imported fire ants currently infest hundreds of millions of acres in southern tier states and Puerto Rico and are spreading northward. As is the case for most exotic species, invasive fire ants were introduced without most of their natural enemies in their native South American range. As a consequence, fire ant populations in the United States are estimated to be about 5-10 times denser than in South America. In recent decades *S. invicta*, for example, has changed from an invasive pest ant in the United States to a global problem, with infestations occurring in Australia, Taiwan, Mainland China, Mexico, and many Caribbean Island countries. This invasive ant is estimated to be responsible for almost $7 billion annually in damage repair, medical care, and control costs in the United States alone. Broad ranging economic sectors are impacted by fire ants including households, electric and communication services, outdoor recreation areas, agriculture, schools, and other areas.

Limited options exist for biologically-based methods of controlling or eliminating invasive and native pest ant populations in urban and rural environments. These limited options are due, in large part, to reliance on conventional pesticides for control, which in turn creates environmental and health risks associated with such pesticides. The use of broad-spectrum, persistent insecticides has significant drawbacks in that the chemicals also kill other beneficial insects and may contaminate surface and ground water due to runoff as well as create other environmental concerns.

There thus exists an industrial, commercial, and public ongoing need to develop efficacious, novel, and safe compositions and control methods to alleviate these problems, particularly for the control of invasive fire ants, as well as other invasive ants and insects, which are also cost-effective and easily adaptable for widespread use.

SUMMARY OF THE INVENTION

To address the challenges in developing biologically-based compositions and methods of controlling insect populations, the present invention accordingly provides novel compositions and uses for the insect neuromodulator tyramine and/or its derivative(s) delivered to insect populations to control certain aspects of those populations. The aspects include, for example, fecundity, reproduction, wing loss, worker lifespan, among others. An aspect of the invention provides compositions for controlling a target population of social insects. The compositions include an effective amount of a compound selected from the group consisting of tyramine, one or more derivatives of tyramine, and combinations thereof. The effective amount in the composition is sufficient to deliver prescribed dosages to the individual insects in the population and control a target population of social insects. In another aspect, the invention provides methods of controlling a population of insects, for example, fire ants. The method includes delivering an amount of tyramine and/or its derivative(s) to the population of insects. The amount of tyramine and/or derivative(s) thereof delivered on a per fire ant basis is greater than a naturally-occurring amount of tyramine normally found in the insects (e.g., within the brains of certain fire ants in the population of fire ants to be controlled). It was surprisingly discovered that delivering such amounts of tyramine and/or its derivative(s) caused mortality of certain insect life forms and disruption of the reproductive capacity of others in the population.

An advantage of the invention is to provide novel and highly effective compositions and methods for controlling social insect populations.

It is an advantage of the invention to provide cost-effective and biologically-based natural compounds to control target populations of fire ants.

It is another advantage of the present invention to provide a novel use of an insect neuromodulator and/or derivative(s)

thereof for controlling target insect populations which has heretofore not been known to have deleterious effects on insect populations.

An additional advantage of the invention is to provide novel methods of controlling target ant populations with a reduced or eliminated need for potentially harmful and dangerous conventional chemical control methods.

It is also an advantage of the current invention to provide methods of controlling target ant populations with compositions that have no known effects on vertebrates.

A further advantage of the invention is to provide methods of controlling target ant populations with compositions that have specificity for particular ant species.

It is a further advantage of the present invention to provide safe and effective methods of controlling insect populations while maintaining ecological integrity.

It is yet another advantage of the present invention to provide environmentally safe and efficacious methods of controlling and/or eliminating fire ant populations using dosages of a conveniently available naturally-occurring ant neuromodulator and/or its derivatives.

Another advantage of this invention is to provide novel biologically-based methods to manage invasive and native pest ant populations in urban and rural environments.

This summary is provided to introduce a selection of concepts in a simplified form that are further described below in the detailed description. This summary is not intended to identify all key or essential features of the claimed subject matter, nor is it intended as an aid in determining the scope of the claimed subject matter.

BRIEF DESCRIPTION OF THE DRAWINGS

FIG. 24A shows worker mortality and FIG. 24B shows queen mortality.

DETAILED DESCRIPTION OF THE INVENTION

Figure 1A:
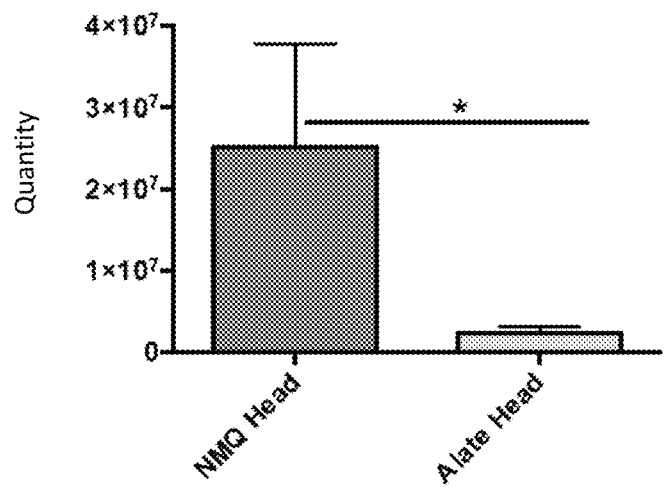
FIG. 1A-1C illustrate quantitative results for tyramine in mature female alate (MFA) and newly mated queen (NMQ) heads, thoraces, and abdomens by HPLC-MS, measured as detector response units.
Figure 1B:
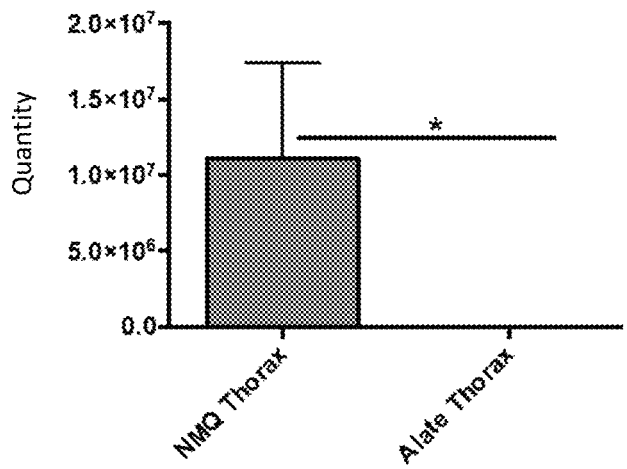
Figure 1C:
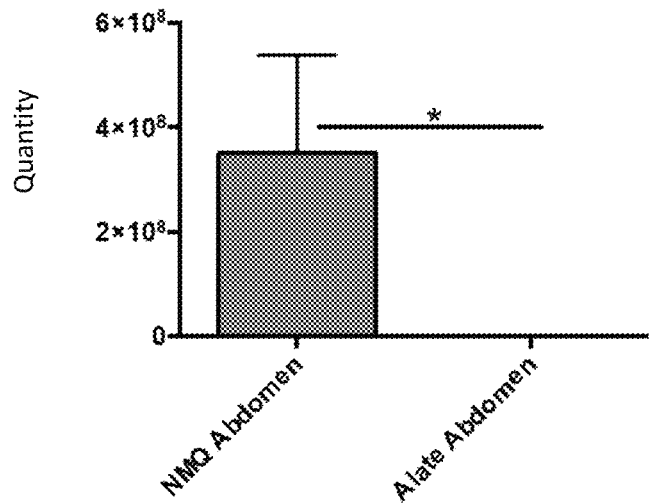

Unless herein defined otherwise, all technical and scientific terms used herein generally have the same meaning as commonly understood by one of ordinary skill in the art to which this invention belongs. Any definitions below may or may not be used in capitalized form herein and are intended to be used as a guide for one of ordinary skill in the art to make and use the invention and are not intended to limit the scope of the invention. Mention of trade names or commercial products is solely for the purpose of providing specific information or examples and does not imply recommendation or endorsement of such products.

The term "consisting essentially of" excludes additional method (or process) steps or composition components that substantially interfere with the intended activity of the method (or process) or composition. This term may be substituted for inclusive terms such as "comprising" or "including" to more narrowly define any of the disclosed embodiments or combinations/sub-combinations thereof.

Furthermore, the exclusive term "consisting" is also understood to be substitutable for these inclusive terms.

The term "effective amount" of a compound or property as provided herein is meant such amount as is capable of performing the function of the compound or property for which an effective amount is expressed. As is pointed out herein, the exact amount required will vary from process to process, depending on recognized variables such as the compounds employed and various internal and external conditions observed as would be interpreted by one of ordinary skill in the art. Thus, it is not possible to specify an exact "effective amount," though preferred ranges have been provided herein. An appropriate effective amount may be determined, however, by one of ordinary skill in the art using only routine experimentation.

The term "optional" or "optionally" means that the subsequently described event or circumstance may or may not occur, and that the description includes instances in which said event or circumstance occurs and instances where it does not. For example, the phrase "optionally comprising a defoaming agent" means that the composition may or may not contain a defoaming agent and that this description includes compositions that contain and do not contain a foaming agent.

The term "substantially pure" refers to a formulation that is at least about 90% (e.g., at least 90%) in purity weight/weight of a total composition. In a more preferred embodiment, the purity is at least about 95% (e.g., at least about 95%) weight-to-weight, or at least about 98% (e.g., at least about 98%) purity.

In invertebrates, the biogenic amines octopamine (OA) and tyramine (TA) are functional homologs to the vertebrate adrenergic neurotransmitters, noradrenaline and adrenaline. They are the only known non-peptide neurotransmitters/hormones found in insects and, interestingly, these biogenic amines have no known activity in vertebrates (see Roeder, T. (2005), Tyramine and octopamine: ruling behavior and metabolism. Ann. Rev. Entomol. 50:447-477) Roeder, Ann. Rev. Entomol. 50:447-477). Biogenic amines are normally biosynthesized and stored in the insect brain. When released into the hemolymph they bind to corresponding G-Protein-coupled receptors (GPCRs) (e.g., tyramine receptor (TAR) and octopamine receptor (OAR)) and elicit a response. As a consequence of the OA and TA invertebrate specificity, there has been research to use the system for insect control through identification of agonists (e.g., to mimic receptor activation) and/or antagonists (e.g., to block the action of the receptor) of the OAR and, to a lesser extent, TAR. TA is the natural ligand for TAR and until the disclosure of this invention, has not been considered to have negative effects on insects.

As described herein, tyramine is normally a neuromodulatory biogenic amines that have been shown to have critical developmental and reproductive functions in insects. Related compounds, tyramides, are found only in males of the ant species in the Myrmicinae sub-family. Tyramides are transferred into the female sexual during mating and are, in turn, quickly hydrolyzed to tyramine (see FIGS. 1A-1C & 2A-2B). Tyramine floods the hemolymph of the now newly mated queen (NMQ) to act on tyramine receptors to trigger wing loss, ovariole development, and other physiological changes in the NMQ quickly after mating. There is no rational linkage between the normal endocrinology of tyramine and the present invention. The discovery that certain dosages of tyramine act to control and/or eliminate populations of fire ants (e.g., killing worker ants) was entirely surprising and unexpected. Also surprising is that tyramine does not have the same impact on all ant species. For example, tawny crazy ant (*Nylanderia fulva*) males do not produce tyramides, but they need to accomplish an analogous result after mating (data not shown). Similar testing with tyramides and tyramine for tawny crazy ant mortality revealed no effect on crazy ant workers (see example 13 below). Additionally, testing fire ants with tyramine and other biogenic amines that may be found in insects (e.g., dopamine, histamine, octopamine, serotonin), surprisingly revealed the desired results specifically with the delivery of tyramine, while the other biogenic amines did not result in significant mortality (see example 12 below). It was equally surprising that tyramine fed to fire ant MFAs by workers in sub-colonies resulted in rapid wing loss and commencement of ovariole development bypassing the normal route of mating flight and mating. In addition, until now ovariole development in MFAs was thought to be held in check by colony queen primer pheromones by inhibition of MFA Juvenile Hormone (JH) release (see Vargo, E. L. (1998), Primer pheromones in ants, pp. 293-313. In R. K. Vander Meer, M. D. Breed, K. E. Espelie and M. L. Winston (eds.), Pheromone communication in social insects ants, wasps, bees, and termites. Westview Press, Boulder, Colo.).

In an embodiment, only tyramine is used in the disclosed methods as the delivered tyramine composition. In other embodiments, tyramine is combined with one or more of its derivatives as the delivered tyramine composition. In yet other embodiments, only one or more tyramine derivatives are used as the delivered tyramine composition. As used herein the term "tyramine" is meant to be inclusive or exclusive according to the context of only (i) tyramine, (ii) tyramine and at least one of its derivatives, or (iii) at least one of its derivatives without the presence of tyramine. For example, tyramine in the absence of its derivatives means the delivery of only tyramine as active ingredient and tyramine and at least one of its derivatives means the delivery of tyramine and one or more of its derivatives as active ingredient. It should be appreciated that any such single active ingredient or combinations of active ingredients may be delivered via any of the mechanisms herein described. Not all tyramine derivatives may exhibit the desired activity and this invention is contemplated to selectively include any one or more of those derivatives of tyramine which exhibit the desired activity or elicit the desired response. There are a number of commercially available tyramine derivatives that may have enhanced activity against fire ants or other pest ants. Among those are, for example, N-(4-chlorobenzoyl) tyramine; N-benzoyl-tyramine; N-formyltyramine; 4-acetlyltyramine; tyramine O-sulfate; 3-fluoro-tyramine; methyl-4-tyramine; 2-tyramine; m-tyramine; 3,5-diiodo-tyramine; N,N-di-n-propyl-m-tyramine; 3-methyl-tyramine; N,N-dimethyl-tyramine; the like; and any combinations thereof. Screening compounds such as these can be carried out by methods already developed for tyramine itself as shown in the examples below.

In an exemplary embodiment, tyramine and/or its derivatives are delivered in a solution or formulation (e.g., sucrose or other formulation attractive to and ingestible by the desired ant population) as an ingestible bait formulation. Sucrose is a food source that induces the ant to ingest it upon tasting it. A substance that induces this type of behavioral action is generally called a phagostimulant. Other examples of fire ant phagostimulants include soybean or corn oil which are used as the active ingredient solvent and phagostimulant. In the present invention, tyramine is water soluble, so the oils may not function as desired unless other additives are used to create an emulsion or make the tyramine miscible or dispersible in the oil. Such methods are known in the art and the particular formulation may be selected by one having skill in the art. In this way, the formulation exerts two major effects: (i) workers and larvae exhibit significant mortality and (ii) female alates in experimental colonies inappropriately exhibit wing loss and begin ovariole development, laying uninseminated eggs which develop into males, and also may produce queen pheromone while in their mother colony. The negative effects of significant mortality are obvious and severely detrimental to colony health. For (ii) the negative effects are two-fold. First, the female alates begin mimicking queens in direct competition with the real queen for colony resources and the eggs they lay are infertile resulting in non-functional males, and second, increased levels of queen pheromone results in lower fecundity of the real colony queen (i.e., colony size decreases).

Not wishing to be bound to a particular theory, the compounds described herein (i.e., tyramine and its derivatives) provide control for ant populations by, for example, disrupting the availability of potential queens, thereby reducing fire ant reproductive potential. In some embodiments, the compositions are used (e.g., applied or devices are deployed) in or prior to the spring season when colonies are producing male and female alates for mating flights. The compounds described herein can also be incorporated into compositions and devices useful in controlling insect pests (e.g., ants such as ants of the subfamily Myrmicinae). For example, the compounds described herein can be incorporated into a composition for application to the environment of the pest, optionally with an agriculturally suitable carrier comprising at least one of a liquid diluent, a solid diluent, or surfactant as further described herein.

In an embodiment, the invention is a method of controlling a population of insects (e.g., a colony or a plurality of colonies of insects including social insects). While it should be appreciated that the method is applicable to a variety of different insects including social insects, the target insect is preferably ants, and, in particular, the method relates to controlling populations of ant species having a functional sting, such as those in the genus *Solenopsis*, one of which is *S. invicta*, known as the "red imported fire ant," and those in the *Myrmica* genus, one of which is *Myrmica rubra*, also known as the European fire ant or common red ant. In embodiments, the compounds, compositions, and formulations described herein can be used in methods for controlling ants, for example, ants of the subfamily Myrmicinae. For example, the methods can be used to control pest species in the following genera: *Monomorium, Myrmicaria, Solenopsis, Megalomyrmex, Trachymyrmex, Cyphomyrmex, Tetramorium, Pheidole, Myrmica, Crematogaster, Pogonomyrmex,* and *Atta*.

The method includes delivering an effective amount of a tryamine composition (the structure of tyramine is shown below) to the population of insects. It should be appreciated, as discussed herein, that the tyramine composition may include tyramine and/or its derivatives as the active ingredient.

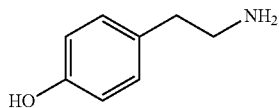

Tyramine and its derivatives are commercially available from a variety of sources. For example, LabNetwork (www-.labnetwork.com), eBiochem (www.ebiochem.com), and Cambridge Chemicals (Boston, Mass.) have tyramine available. In addition, methods of synthesizing tyramine and its derivatives are known in the art (see e.g., Shimizu, Y., et al., (2012), Microwave-Assisted Deacylation of Unactivated Amides Using Ammonium-Salt-Accelerated Transamidation. *Angew. Chem. Int. Ed.,* 51: 8564-8567; Zhang, H., et al., (2016), Two-step enzymatic synthesis of tyramine from raw pyruvate fermentation broth. *J. Mol. Catal. B: Enzym.,* 124: 38-44; Santaniello, E., et al., (1981), On the stereochemistry of the decarboxylation of (2S)-histidine catalysed by histidine decarboxylase from *Clostridium welchii* (E.C.4.1.1.22). *J. Chem. Soc., Perkin Trans.* 1, 307-309; Rastetter, W. H. and Nummy, L. J. (1980), epidithiadiketopiperazines. Biogenesis of Synthesis of the three isomeric (.beta.-aminoethyl)benzene oxides. *J. Org. Chem.,* 45(16): 3149-3155).

In embodiments, the invention is a composition including an effective amount of a compound selected from the group consisting of: tyramine, one or more derivatives of tyramine, and combinations thereof. The effective amount is sufficient to control a target population of social insects and is described herein in relation to the treatment methods for the target population(s) of social insects. The composition may include one or more various liquid diluents, solid diluents, surfactants, additives, preservatives, and combinations thereof as described herein. The composition may be in the form of a substantially pure composition, or, in other embodiments as a solid, liquid, semi-solid, spay, powder, granule, tablet, gel, cream, lotion, the like, and combinations thereof as further described below.

The effective amount of tyramine delivered to the population may be calculated as a multiple of the amount on a per insect basis (e.g., worker ant, fire ant worker) of an average amount of naturally-occurring tyramine in individual insects, such as within the brains or other parts of individual insects (e.g., worker ant, fire ant worker). For example, it is estimated that "normal" fire ant workers have an amount of tyramine in their brains ranging from about 250 picograms to about 600 picograms (e.g., individual fire ant worker brains contain about 250 pg of octopamine on average and about 600 pg of dopamine on average (see Vander Meer, R. K., et al., (2008), Queen regulates biogenic amine level and nestmate recognition in workers of the fire ant, *Solenopsis invicta*. Naturwissenschaften 95(12): 1155-1158). Fire ant sexual larvae die when fed 0.8 micrograms tyramine and it is estimated from feeding studies (see examples below) that 0.01 micrograms per microliter solution of tyramine fed to workers led to mortality after 7 days. These values were empirically obtained and are much greater than the naturally occurring amount. An effective amount of tyramine delivered to an insect population is, therefore, preferably from about 0.01 microgram to about 2.0 micrograms (e.g., 0.01 microgram to 2.0 micrograms) of tyramine active ingredient per fire ant worker, according to an embodiment. A preferred range of tyramine active ingredient is from about 0.1 micrograms to about 2 micrograms (e.g., 0.1 microgram to 2 micrograms), or from about 0.2 microgram to about 3 micrograms (e.g., 0.2 microgram to 3 micrograms), or from about 0.3 microgram to about 4 micrograms (0.3 microgram to 4 micrograms) per fire ant worker. It should be appreciated that much higher amounts of tyramine and/or its derivatives could also be delivered to the insect population (e.g., 2 to 5 micrograms, 5 to 10 micrograms, 10 to 20 micrograms per fire ant worker, or higher).

In an embodiment, the amount of tyramine effective to produce the surprising and unexpected results of the invention may also be calculated as a multiple of the amount of tyramine present in the brain of an individual insect (e.g., ant, worker ant, fire ant worker). In a preferred embodiment, the amount of total tyramine delivered to a population is equivalent to at least about 1,000,000 (e.g., 1,000,000) times the amount of tyramine present on average on a per insect basis within the population, or at least about 100,000 (e.g., 100,000) times, or at least about 50,000 (e.g., 50,000) times, or at least about 25,000 (e.g., 25,000) times, or at least about 10,000 (e.g., 10,000) times, or at least about 1,000 (e.g., 1,000) times, or at least about 500 (e.g., 500) times, or at least about 100 (e.g., 100) times, or at least about 50 (e.g., 50) times, or from about 50 to about 1,000 times (e.g., 50 to 1,000), or any value within such ranges as selected by a skilled artisan. For example, if an individual fire ant worker has from about 250 picograms to about 600 picograms of tyramine in its brain and there are 50,000 fire ant workers in the population, the amount of tyramine active ingredient delivered would be at least about 0.05 grams. For another example, 1.25 grams could be used for 50,000 fire ant workers to deliver about 25 micrograms per worker (or about 25,000,000 picograms per worker). This delivered amount is about forty two thousand times the 600 picogram maximum value normally found in a worker ant brain. If one microgram was needed per worker for a particular target population, 50,000 workers would ingest a total of about 50 mg of tyramine or 0.05 g.

The amount of active ingredient in the compositions of the invention is/are present in an amount sufficient to deliver the prescribed dosages to the insect populations based on, for example, an amount to be delivered to a target insect population on a per insect basis and/or a concentration range of the active ingredient. A preferred concentration for the active ingredient of tyramine and/or derivatives thereof is at least about 0.0001% on a weight per volume basis, or a range from about 0.0001% (e.g., 1,000 pg/µl) to about 1% (e.g., 1 mg/ml) on a weight per volume basis, or from about 0.001% to about 1%, or from about 0.01% to about 1%. Higher concentrations may also be used but are generally not usable due to the solubility limitations of tyramine and derivatives thereof in aqueous solutions. The composition may also be prepared from a more concentrated form such as a solid or powder. For example, the active ingredient may be mixed with a solid diluent or in combination with a phagostimulant which the user would mix with an aqueous diluent to produce a phagostimulant. In another example, tyramine and/or its derivatives could be pre-formulated with the appropriate amount of phagostimulant (e.g., sucrose or other phagostimulants selected by a skilled artisan for a particular application) in a sachet or other container that would preserve its integrity until use for pest ant control. The sachet could be opened and poured into the correct pre-measured amount of an aqueous diluent. Alternatively, the sachet type is selected from a variety of materials, such as biodegradable or bio-based plastic. In another example, the sachet is water-soluble plastic which could dropped into a pre-measured amount of water to achieve an aqueous composition having the desired concentration. The solution would then be used to charge a bait station dispenser (discussed below). The bait station dispenser could be charged as needed with a freshly prepared composition as often as needed. As further discussed herein, another embodiment of the solid ingredients is tyramine combined with phagostimulant and optional preservative. Compatibility of such ingredients would be determined for a given application by a skilled artisan. In another embodiment, the aqueous formulation comprises tyramine and/or its derivative combined with a phagostimulant and an optional preservative which is then absorbed into an inert material or matrix from which the target insect could access the liquid from the inert material. In a further embodiment, the liquid formulation could be encapsulated (e.g., hydrogels or other such material as discussed below). The sachet or encapsulating material containing the composition may be of such construction that the target insect could sense the phagostimulant and break open the encapsulation to access the composition within the capsule or sachet.

The formulation or composition ingredients are selected to be consistent with the physical properties of the active ingredient, mode of application (e.g., bait design or bait station type) and environmental factors such as soil type, moisture, and temperature. Useful formulations include liquids such as solutions (e.g., including emulsifiable concentrates), suspensions, emulsions (e.g., including microemulsions and/or suspoemulsions) and the like which optionally can be thickened into gels. Useful formulations further include solids such as dusts, powders, granules, pellets, tablets, films, and the like which can be water-dispersible (e.g., wettable) or water-soluble. Active ingredient can be encapsulated or microencapsulated and further formed into a suspension or solid formulation; alternatively the entire formulation of active ingredient can be encapsulated or microencapsulated (e.g., to control or delay release of the active ingredient). Sprayable formulations can be suspended in suitable media and used at preferred spray volumes (e.g., from about one to several hundred liters per hectare). High-strength compositions are primarily used as intermediates (e.g., concentrates) for further formulation (e.g., by dilution).

Solid diluents are known in the art (e.g., as described in Watkins, et al., Handbook of Insecticide Dust Diluents and Carriers, 2nd Ed., Dorland Books, Caldwell, N.J.). Exemplary solid diluents can include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents are known in the art (e.g., as described in Marsden, Solvents Guide, 2nd Ed., Interscience, New York, 1950). Exemplary liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tong, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol, and tetrahydrofurfuryl alcohol.

Surfactants are known in the art (e.g., as described in McCutcheon's Detergents and Emulsifiers Annual, Allured Publ. Corp., Ridgewood, N.J.; and in Sisely and Wood, Encyclopedia of Surface Active Agents, Chemical Publ. Co., Inc., New York, 1964). Surfactants can include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers.

In some embodiments, the formulations described herein can contain minor amounts of additives to reduce foam, caking, corrosion, microbiological growth and the like, or thickeners to increase viscosity. Methods for preparing the formulations described herein are known in the art. For example, solutions, including emulsifiable concentrates, can be prepared by simply mixing the ingredients. Dusts and powders can be prepared (e.g., by blending and, optionally grinding such as using a hammer mill or fluid-energy mill). Suspensions can be prepared, for example, by wet-milling (see e.g., U.S. Pat. No. 3,060,084). Granules and pellets can be prepared by, for example, spraying the active material upon preformed granular carriers or by agglomeration techniques (see e.g., Browning, Chem. Eng., p 14748, (1967); Perry's Chemical Engineer's Handbook, 4th Ed., McGraw-Hill, New York, 1963, pages 8-57 and following, and PCT Publication WO 91/13546). Pellets can be prepared using methods known in the art (e.g., as described in U.S. Pat. No. 4,172,714). Water-dispersible and water-soluble granules can be prepared (e.g., as taught in U.S. Pat. Nos. 4,144,050, 3,920,442 and DE 3,246,493). Tablets can be prepared (e.g., as taught in U.S. Pat. Nos. 5,180,587, 5,232,701, 5,208,030, 6,245,816, or 7,696,233; or see also Woods, "The Formulator's Toolbox—Product Forms for Modern Agriculture" in Pesticide Chemistry and Bioscience, The Food—Environment Challenge, T. Brooks and T. R. Roberts, Eds., Proceedings of the 9th International Congress on Pesticide Chemistry, The Royal Society of Chemistry, Cambridge, 1999, pp. 120-133).

In embodiments, the composition can be delivered in a solid (e.g., as pellets or powder formulation); a semi-solid (e.g., a gel, hydrogel, or gellable formulation), as part of an ant trap; or in a liquid formulation (e.g., in a spray format), and can be used, for example, to attract, direct, or repel ants from or to a selected area. In some embodiments, the compounds described herein are used as a repellent (e.g., applied to or in an area in which the presence of ants is not desired). The area can be, for example, an indoor or outdoor area, in which case the compounds can be delivered generally (e.g., in a spray, powder, granule, gel, hydrogel, or other format). In some embodiments, the composition can be provided in a delayed-release composition (e.g., any method of dispersal, dispensation, application, timed-release, encapsulation, microencapsulation, or the like to apply the composition of the invention as further described herein). In embodiments, "carriers" may include a variety of microencapsulation, controlled-release, and other dispersion technologies available to those of ordinary skill in the art, so that the composition is released over time. Other suitable compositions are also known in the art.

In some embodiments, the compounds described herein can be formulated with other ingredients (e.g., ant-attractant or ingredients such as one or more phagostimulants, ant food (e.g., carbohydrates, fats, proteins, and/or any other nutritional components), etc. (see, e.g., U.S. Pat. Nos. 5,152,096; 5,939,061; 6,916,469; and 7,048,918)). Preferred concentrations of sugar in, for example, an ingestible bait composition is from about 1% to about 5% (e.g., 1% to 5%), or from about 5% to about 10% (e.g., 5% to 10%), or from about 10% to about 50% (e.g., 10% to 50%) sugar weight-to-weight. High concentrations of sugars, for example, have antimicrobial properties. For example, a 10% sucrose solution as used in the examples below retarded formation of a color in the solution for about a week (data not shown). Increasing the concentration to 50% gave microbial control for about 3 weeks; however, such high levels of sucrose decrease the amount of solution ingested. A 1% solution of the disclosed active compounds (e.g., tyramine or N-methyl tyramine) is at their solubility maximum. Keeping sucrose levels lower (e.g., about 10%) and adding a non-nutritive antimicrobial preservative to increase the lifetime of the solution at ambient temperatures would be beneficial in alternative embodiments of the invention. Examples of preservatives are known in the art and may be selected as needed by a skilled artisan in implementing the invention: citric acid, ascorbic acid, sodium nitrite, sulfites (e.g. sulfur dioxide), and sodium erythorbate The compounds described herein can be formulated or emulsified/homogenized, for example, as part of an ant bait to deliver an ant toxin for extermination of pest insects. A number of ant toxins are known in the art, including Thiamethoxam (Syngenta Crop Protection, Greensboro, N.C.); DOT; growth regulators; orthoboric acid; borates (e.g., sodium tetraborate); abamectin BI (Whitmire Micro-Gen Research Laboratories, Inc.); fipronil (2-Phenethyl Propionate); Sulfluramid; Imidacloprid (Bayer Environmental Science, Montvale, N.J.); indoxacarb (Dupont, Wilmington, Del.); O,S-Dimethyl Acetylphosphoramidothioate; 2-phenethyl propionate; piperonyl butoxide; pyrethrins (e.g., permethrin, deltamethrin, tetramethrin, or Lambda-cyhalothrin [1.alpha.(S*),3.alpha.(Z)]-(.+-.)-cyano-(3-phenoxyphenyl) methyl-3-(2-chlo-ro-3,3,3-trifluoro-1-propenyl)-2,2-dimethylcyclopropanecarboxylate); or Cry toxin (U.S. Pat. No. 6,797,490). The toxin can be delivered with the compounds described herein (e.g., as part of a single composition) or can be delivered before or after delivery of the compounds described herein. In embodiments, the disclosed tyramine composition may be delivered as part of a solution such as a sugar solution (e.g., sucrose, glucose, fructose, and the like). Sucrose is a very good fire ant worker phagostimulant and also has antimicrobial activity, exerted via high osmotic pressure. The higher the concentration the greater the osmotic pressure and the better the antimicrobial activity.

In some embodiments, the compounds described herein are used with an insect trap (e.g., to attract and trap insects) for pest control or to detect new or ongoing infestations. The traps can optionally include means for preventing the insect from escaping the trap. For example, mechanical traps are generally designed to physically prevent the insect from leaving, such as a pattern that only allows ingress but not egress, or an edge or flange that prevents escape. Chemical traps having, for example, an adhesive or liquid that traps the insect, may also be used. Other examples are described in U.S. Pat. Nos. 6,966,145, 6,609,330, 6,796,082, 6,283,064, 6,655,079, 6,474,015, 5,746,021, and 5325626. Other suitable traps are also known in the art.

In general the present formulations and compounds will be delivered in an amount effective for the intended purpose for insect control and can be delivered directly onto an area known or evident of infestation (e.g., targeted directly onto an ant colony, or near an area known or suspected of ant infestation). In embodiments, the disclosed compositions are delivered onto an agricultural (e.g., hundreds or thousands of acres), residential (e.g., over less than acre or up to tens of acres), or commercial area in which ant control is desirable. Various modes of delivery may be used as herein described. For example, bait stations are known in the art and a skilled artisan would select an appropriate bait station or bait design for any set of circumstances where the invention is to be deployed and used (see e.g., U.S. Pat. Nos. 5,939,061; 5,746,021; 7,941,777). Furthermore, the invention also provides kits which are useful for carrying out methods of the present invention. The kit includes a container comprising compositions of the present invention and instructions for using the compositions for the purpose of controlling insect populations as disclosed herein. The kits can comprise a first container means containing the compositions described herein. The kit can also comprise other container means having one or more solutions, diluents, or applicators necessary or convenient for carrying out the invention. The container means can be made of glass, plastic, foil, the like, and combinations thereof and can be any suitable vial, bottle, pouch, tube, bag, box, etc. The kit can also contain written information, such as procedures for carrying out the present invention or analytical information, such as the amount of reagent contained in the first container means. The container means can be in another container means (e.g., a box, bag, etc.) along with the written information.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement. The following examples are intended only to further illustrate the invention and are not intended in any way to limit the scope of the invention as defined by the claims.

Example 1

Analysis of mature female alate (MFA) and newly mated queen (NMQ) heads, thoraces, and abdomens by HPLC-MS for tyramine yielded the quantitative results shown in FIG. 1. The Y-axis Units are detector response. The amount of tyramine within the three graphs are comparable via the mean detector response value. Note that the Y-axis scale is different in the three graphs and that the amount of tyramine in NMQ abdomens is about 20 to 30 times the amount in NMQ heads and thoraces. The amount of tyramine in NMQs is significantly greater than the amount found in MFAs for all body parts. The time from an MFA to NMQ during the mating flight is only about 60 min and the NMQs collected for this analysis were refrigerated or frozen within 30 min of collection. Previous research demonstrated that males store microgram quantities of acetyl and hexanoyl tyramides in their external genitalia, and that they transfer these compounds to MFAs during the mating process (data not shown). These two pieces of information led to the hypothesis that MFAs have enzymes in their reproductive system that hydrolyze tyramides to tyramine, which then passes into the now NMQ's hemolymph to act on tyramine receptors.

Example 2

Figure 2A:
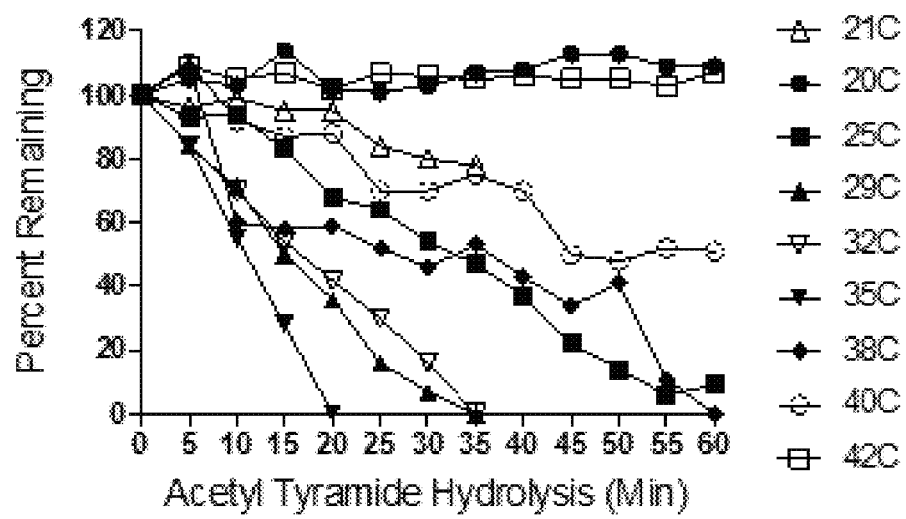
FIG. 2A-2B shows data for establishing the enzymatic hydrolysis of acetyl and hexanoyl tyramide via enzymes found in the MFA reproductive system.
Figure 2B:
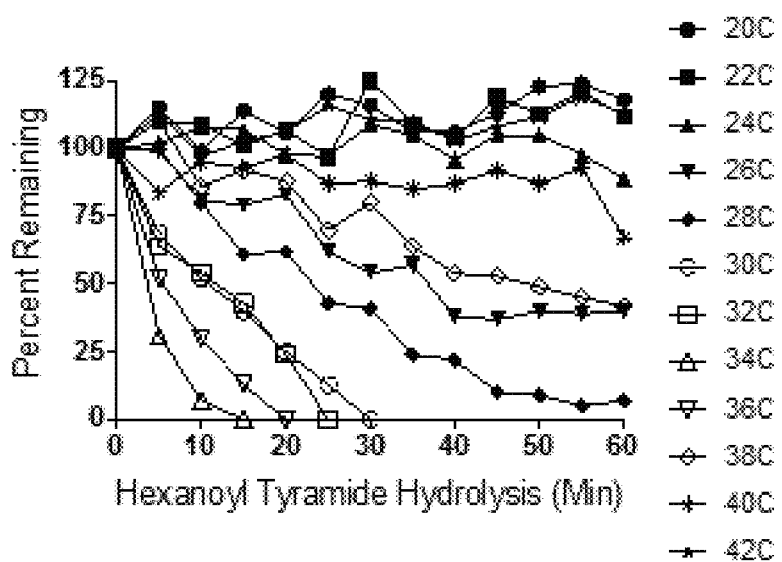

To test the enzymatic hydrolysis hypothesis discussed in Example 1, the tip of the MFA reproductive system was dissected, sonicated in water, then a known amount of synthetic tyramide was added and incubated at a single temperature (see FIG. 2A-2B) for 60 min. Aliquots were removed at 5 min intervals and added to methanol to quench the enzymatic reaction, then analyzed for tyramide by GC/MS. As shown in FIG. 2A-2B, temperatures from 20° C. to 42° C. defined the temperature dependence of the enzyme. At the end of these experiments, the remaining extract was analyzed for tyramine (HFBAA derivatization—see Vander Meer, R. K., et al., (2008), Queen regulates biogenic amine level and nestmate recognition in workers of the fire ant, *Solenopsis invicta*. Naturwissenschaften 95(12): 1155-1158)) and Expression CMS (Compact Mass Spectrometer) (Advion Biosciences Inc., Ithaca, N.Y.). The results confirmed that the tyramides were being converted to tyramine. To determine the specificity of this enzyme MFA mid- and hind-gut were dissected, sonicated in water, acetyl or hexanoyl tyramide was added, and incubated at 32° C. Samples were taken periodically as described above (data not shown). No degradation of the tyramide was observed, therefore, the tyramide hydrolase is specific to the MFA reproductive system.

Example 3

Figure 3A:
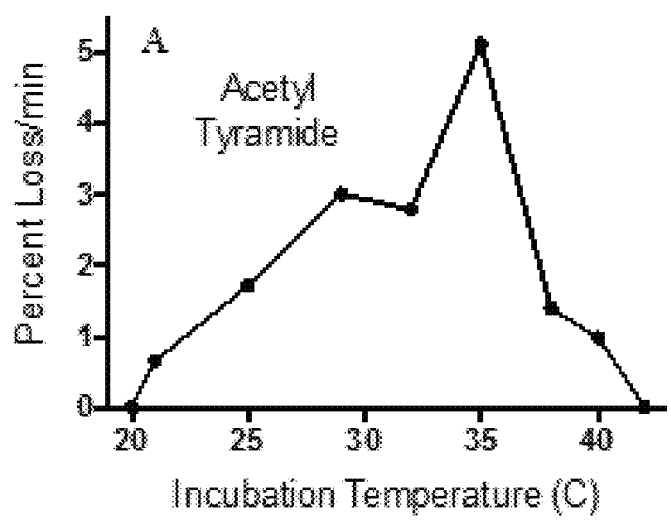
FIG. 3A-3B shows the percent loss of acetyl and hexanoyl tyramide over time when incubated with tyramide hydrolase.
Figure 3B:
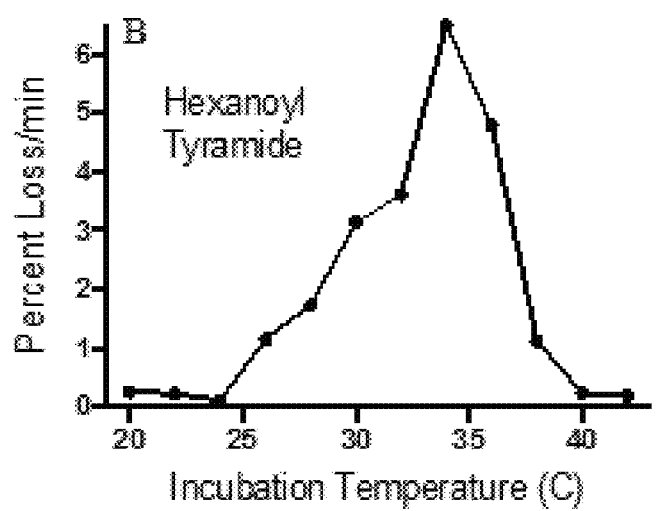

The graphs in FIGS. 3A and 3B were converted to percent loss to normalize differences in initial tyramide concentration, then subjected to linear regression to provide the slopes (i.e., rate of loss) for each incubation temperature. FIGS. 3A and 3B show the percent loss of acetyl and hexanoyl tyramide over time (shown in min). It is clear that the tyramide hydrolase has a window of activity between 20° C. and 40° C. for the acetyl tyramide and between 24° C. and 40° C. for hexanoyl tyramide. The male fire ant transfers both tyramides to the female, but upon hydrolysis both tyramides are converted to tyramine. These temperature ranges closely correspond to mating flight temperatures reported in the literature (see e.g., Tschinkel W R. The fire ants. Cambridge, Mass.: Harvard University Press; 2006. p. 747), suggesting close evolutionary coupling of the enzyme and mating flight activity.

Example 4

Figure 4A:
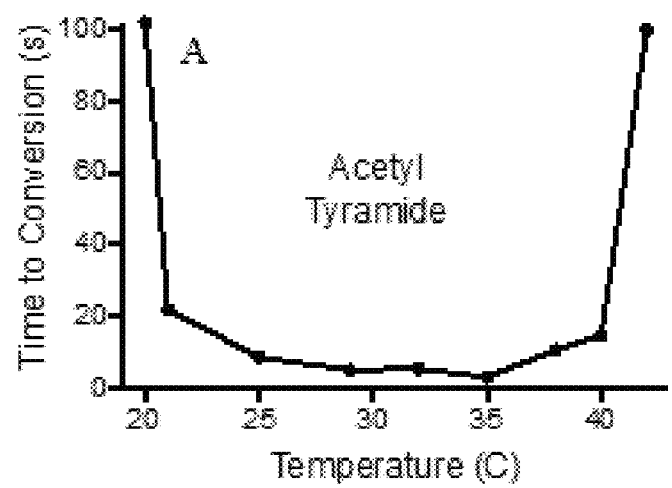
FIG. 4A-4B shows hydrolysis and temperature range for efficient conversion of acetyl and hexanoyl tyramides to tyramine, which corresponds to fire ant mating flight temperatures.
Figure 4B:
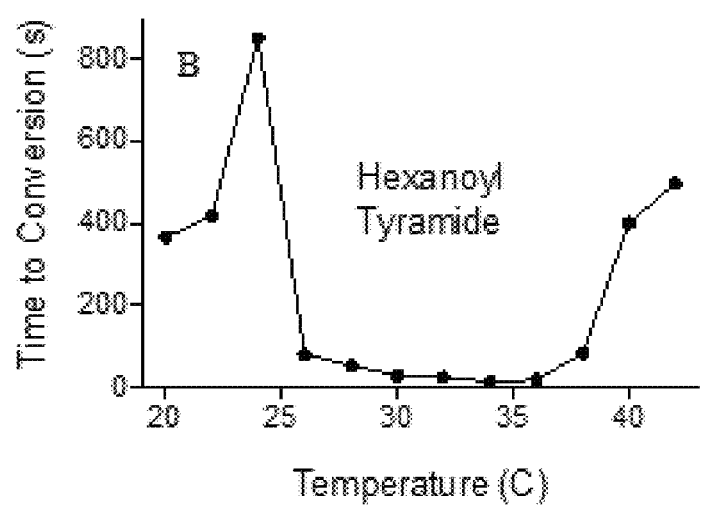

The rate of loss illustrated in FIG. 3A-3B provides the data necessary to calculate (under the experimental conditions indicated in Example 3) the time it would take the NMQ to hydrolyze the mean amount of the two tyramides in male external genitalia (FIG. 4A=3.0 microgram and FIG. 4B=3.5 microgram), previously determined (unpublished data, Vander Meer, 2015). The graphs clearly show very rapid hydrolysis and a clear temperature range for most efficient conversion of the tyramides to tyramine. The actual rate of conversion may be modulated by other compounds or sperm also being transferred to the MFA during mating.

Example 5

Figure 5A:
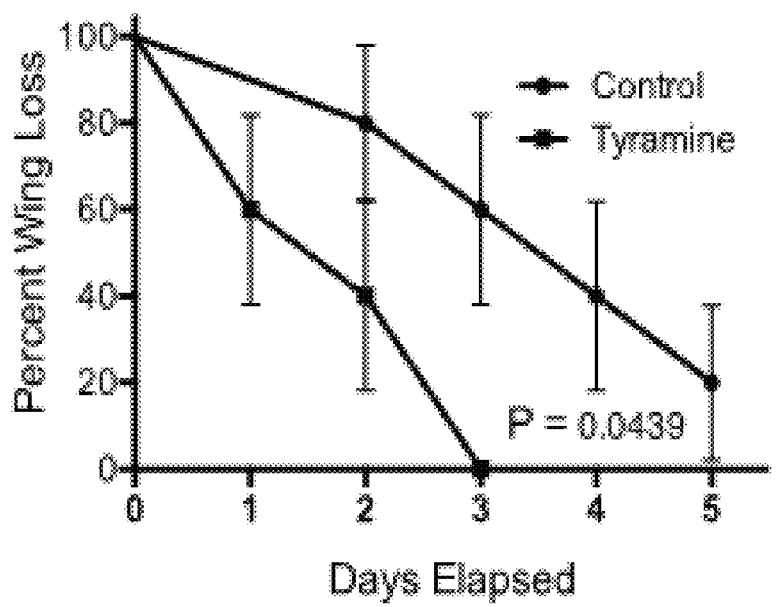
FIG. 5A-5B show phenotypic effects of tyramine and acetyl tyramide on MFAs after injection, including an illustration that injection of tyramine (5A) or acetyl tyramide (5B) causes faster and inappropriate dealation in MFAs, when compared to the control.
Figure 5B:
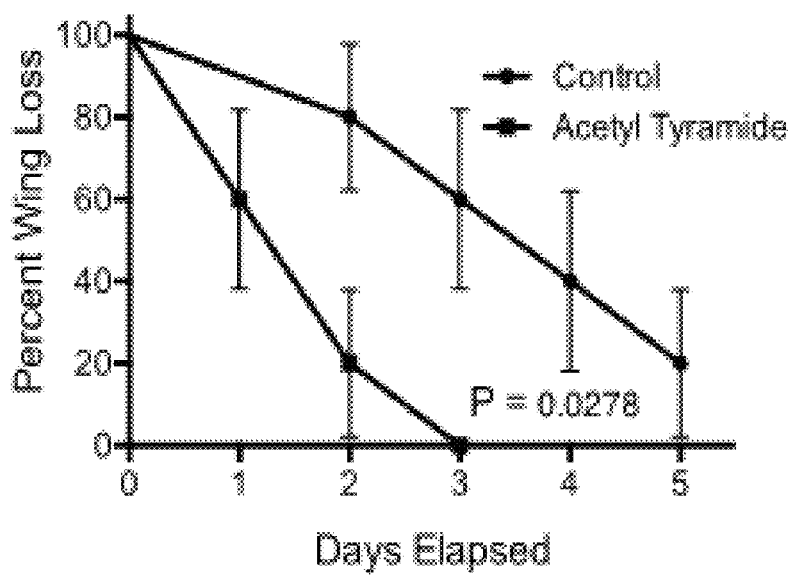

While the MFAs are in their mother colony, the queen releases primer pheromones that inhibit wing loss (sometimes referred to herein as "dealation"), development of ovaries, wing muscle histolysis, and pheromone production. This release prevents reproductive/resource competition between the MFAs and the mother queen. If MFAs are removed from the colony, they become disinhibited and eventually (e.g., within days) lose their wings and start the physiological processes (e.g., wing loss and ovariole development). MFA also become disinhibited when they leave the colony on a mating flight; however, in this case the now NMQs lose their wings within minutes of landing and initiate the above mentioned physiological/biochemical changes (e.g., wing loss and ovariole development). We know from previous experiments that mating is the trigger, not mating flight initiation or the act of flying (Burns, S. N., et al. (2002) Identification and action of juvenile hormone III from sexually mature alate females of the red imported fire ant, *Solenopsis invicta*. Journal of Insect Physiology 48: 357-365; Burns, S. N., et al. (2005), The effect of age and social environment on dealation in *Solenopsis invicta* (Hymenoptera: Formicidae) female alates. Florida Entomologist 88(4): 452-457; Burns, S. N., et al. (2007), Mating flight activity as dealation factors for fire ant, *Solenopsis invicta*, female alates. Annals of the Entomological Society of America 100(2): 257-264). Testing was performed to determine whether the male-derived tyramides and/or their NMQ hydrolysis product, tyramine, are the causative agent(s) that initiate wing loss and the associated physiological changes that occur in NMQs. FIG. 5A-5B show phenotypic effects of tyramine and acetyl tyramide on MFAs after injection (100 nL of a 1.0% saline solution injected into the MFA abdomen using a nano-injection system, Bioquip Products, Compton Calif.). Wing loss (dealation) for female alates typically occurs soon after mating. Injection of tyramine (5A) or acetyl tyramide (5B) causes significantly faster and inappropriate dealation (not caused by mating process) in female alates, when compared to the control.

Example 6

Figure 6A:
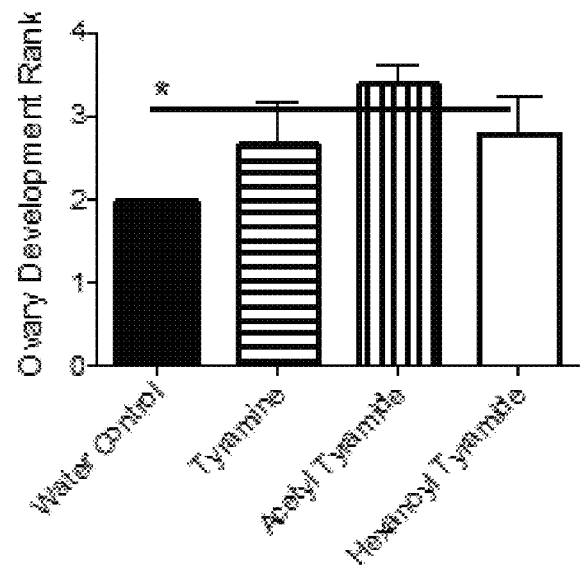
FIG. 6A-6B show the effect of water control, tyramine, acetyl tyramide, and hexanoyl tyramide on ovariole development when injected into MFAs.
Figure 6B:
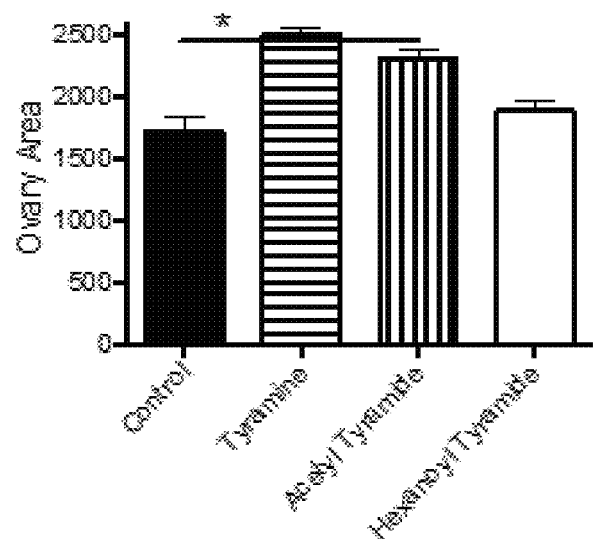

FIG. 6A-6B show the effect of water control, tyramine, acetyl tyramide, and hexanoyl tyramide on ovariole development when injected into MFAs (100 nL of a 1.0% saline solution (1 microgram) injected into the MFA (unpublished, Vander Meer 2015) abdomen (about 50% of what the males have available to transfer to the MFA are using a nano-injection system, Bioquip Products, Compton Calif.). Two measures of ovariole development were used. In FIG. 6A control and treatment ovarioles were compared to a series of 4 ovary-ranking photos where a rank of 1 was the least developed and a rank of 4 was the highest. It was surprisingly discovered that injection caused significant ovariole development in all treatments compared to the control, FIG. 6A. Measurement of ovariole area in the same samples gave a quantitative measure of ovariole development. Tyramine and acetyl tyramide, but not hexanoyl tyramide caused significant ovariole development compared to controls, FIG. 6B. In addition, injection surprisingly initiated inappropriate egg-laying by the treated female alates—sometimes surprisingly coupled with dealation and sometimes independent of dealation. Within the context of a colony this effect would be in direct conflict with the colony queen. Eggs laid would not be fertile and therefore develop into males. Queen pheromone is also produced by dealates, which would act to reduce the fecundity of the colony queen. For example, in polygyne colonies the higher the number of queens the lower is the mean egg-laying rate/queen due to the presence of excess queen pheromone (see Vander Meer, R. K., et al. (1992), A comparison of queen oviposition rates from monogyne and polygyne fire ant, *Solenopsis invicta*, colonies. Physiological Entomology 17(4): 384-390).

Example 7

Figure 7:
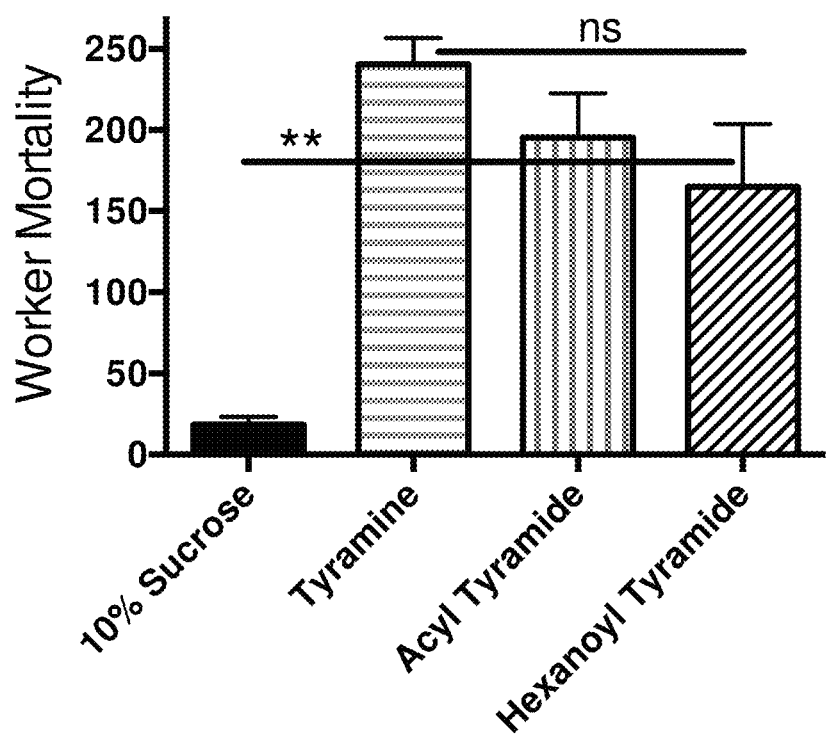
FIG. 7 shows accumulated worker mortality after feeding on a sucrose solution containing tyramine or tyramides.

For commercial use of controlling social insect populations, the compounds must show phenotypic effects through feeding, as is necessary for bait development. Baits take advantage of the insects (e.g., fire ants) excellent resource recruitment system that requires less active ingredient and the user does not have to locate all colonies if the bait is distributed on the general foraging surface or distributed in bait stations. Experiments were designed to detect phenotypic effects induced through feeding tyramides and tyramine to fire ants. The experimental units were queen-right sub-colonies (i.e., queen (polygyne), brood and workers). Workers were allowed to feed on a 10% sucrose solution as control or with approximately 1% (w/v) of the tyramides or tyramine. FIG. 7 shows accumulated worker mortality at 9 days after start of experiment. Surprisingly high worker mortality was observed from each of the three treatments (ns=not significant), thus the treatments were not significantly different from each other. However, all treatments were significantly different from the sucrose controls (t-test, unpaired, parametric, 2-tailed, P=0.0029). The starting number of workers was about 300, and in some replicates very few workers were left to tend the queen and brood.

Example 8

Figure 8A:
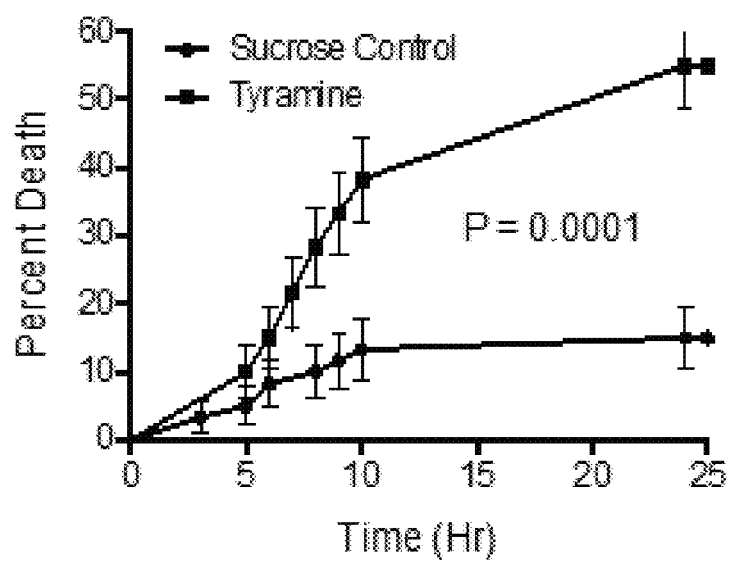
FIG. 8A-8B shows worker mortality after feeding on a sucrose solution containing tyramine or acetyl tyramide in fully functional sub-colonies.
Figure 8B:
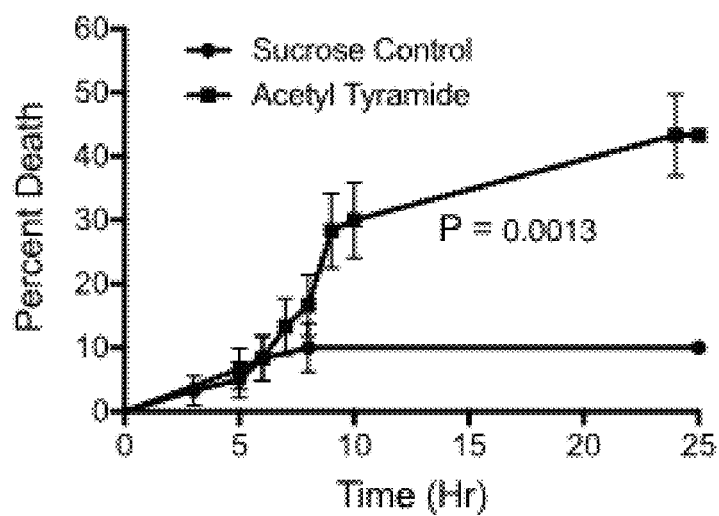

To determine how quickly the tyramine and acetyl tyramide act, 60 workers were allowed to feed on tyramine (FIG. 8A) or acetyl tyramide (FIG. 8B) dissolved at about 1% in 10% sucrose solution. The control and treatments were presented to the worker ants as droplets on phase separation filter paper. Consumption of the droplets was readily observed. Mortality was monitored for each of the first 10 hours and then at 24 hours. As seen in FIGS. 8A and 8B, both treatments had significantly greater worker mortality than the sucrose control (Kaplan-Meier mortality curve, Log-rank, Mantel-Cox test). Tyramine and acetyl tyramide had >50% and >40% mortality, respectively within the 24 h time period of the experiment. The observed rapid mortality and potential abnormal behavior before death suggested that the fed workers might not distribute the ingested sucrose solution to their nestmates as would normally be the case. This distribution is a cornerstone of pest ant baits. To test this hypothesis, a similar experiment was conducted. Workers were allowed to feed on the treatment and control solutions and were then transferred to another container with unfed nestmates. In all cases, it was observed that the treatment fed workers regurgitated the treatment and sucrose solutions to their unfed nestmates through the classic mechanism of trophallaxis (data not shown). Thus, normal worker behavior necessary for bait development was not affected by the treatments under these experimental conditions.

Example 9

Figure 9A:
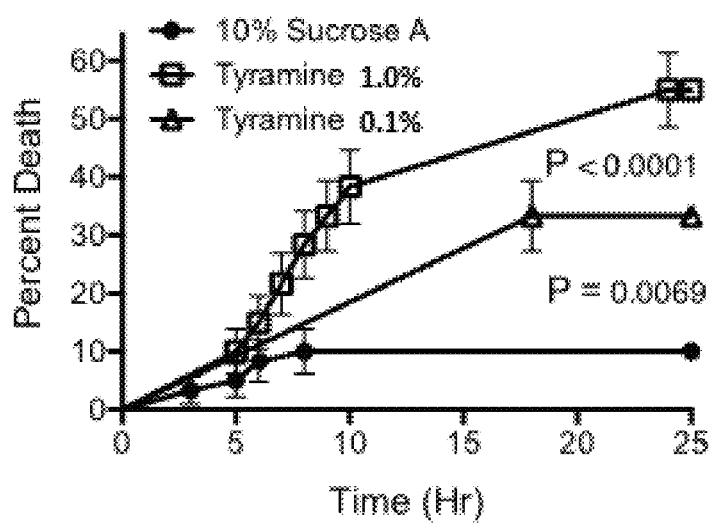
FIG. 9A-9B shows worker mortality for three concentrations of tyramine fed as droplets to worker groups.
Figure 9B:
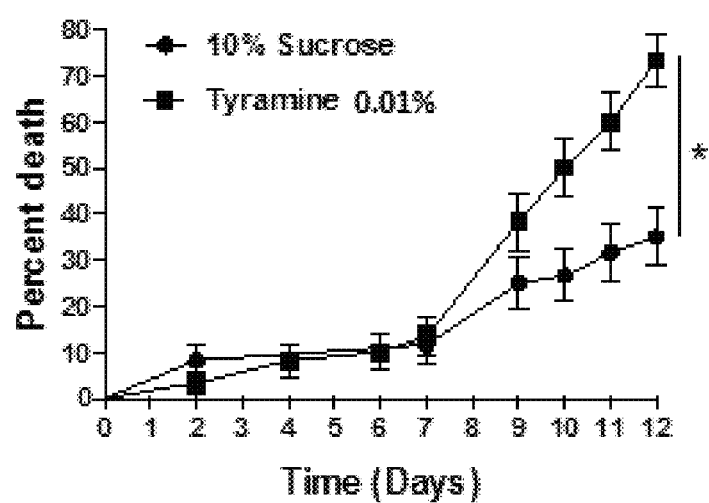

One criteria for an effective pest ant Active Ingredient (AI) is maintenance of activity over 1-3 orders of magnitude, because as the bait is distributed from one ant to another the material is diluted. The AI must maintain activity until all individuals in the colony (e.g., workers, brood and sexuals including the queen) have received the AI. FIG. 9A-9B shows three concentrations of tyramine (about 1.0, 0.1, and 0.01% (weight-to-volume) fed to worker groups as described above. Kaplan-Meier mortality curves are shown in FIG. 9A-9B. It was surprisingly observed that significant worker mortality is observed even at a dilution factor of 100 (FIG. 9B, Log-rank, Mantel-Cox test). Similar results were observed for acetyl tyramide and to a lesser extent hexanoyl tyramide. Delayed AI activity is an important factor for ant baits. The 1.0 and 0.1% concentrations had at least a 5 h mortality delay which is likely enough to allow complete distribution of the bait throughout the colony life forms (Oi, D. H., et al. (2006), Speed of efficacy and delayed toxicity characteristics of fast-acting fire ant (Hymenoptera: Formicidae) baits. Journal of Economic Entomology 99(5): 1739-1748). The 0.01% had >24 h delay in mortality.

Example 10

Figure 10:
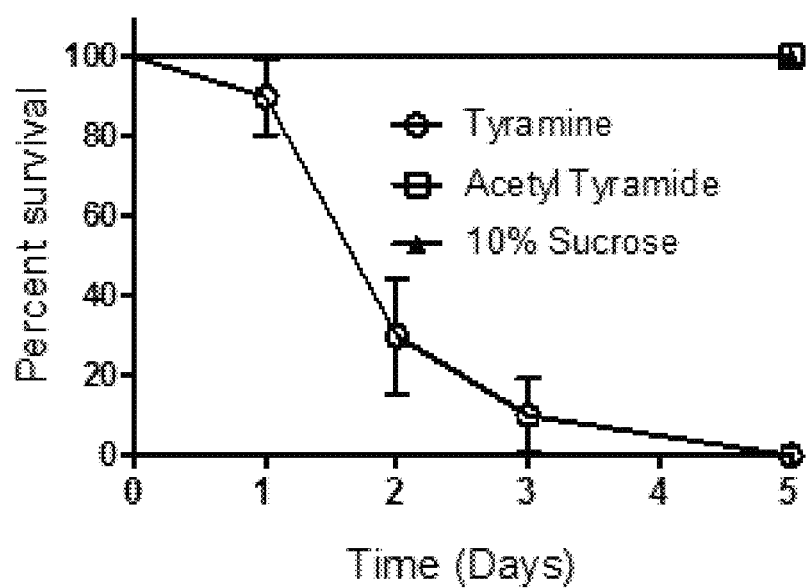
FIG. 10 shows the effects of tyramine and acetyl tyramide hand fed to larvae.

To determine the effects of tyramine and the acetyl tyramide on larvae, a bioassay was developed and used that allowed direct feeding of 4th instar (i.e., last instar) sexual larvae known amounts (80 nL max) of test solutions (treatments were at close to near-maximum soluble concentration (about 1% weight-to-volume) in a 10% sucrose solution (weight-to-volume). Fourth instar sexual larvae were used because worker 4th instar larvae are too small to avoid over feeding, which usually results in death. Larvae (N=10) were fed once, then observed for phenotypic effects (FIG. 10). Surprisingly, after day one of the tyramine treatment the surviving larvae appeared sick and started to ooze fluid. All sexual larvae fed tyramine died by day 5. None of the controls died during this time period, but surprisingly, none of the acetyl tyramide treatments died or appeared sick. It was concluded that the 4th instar larvae are refractory to the mortality effects observed when workers are fed tyramine.

Example 11

Figure 11A:
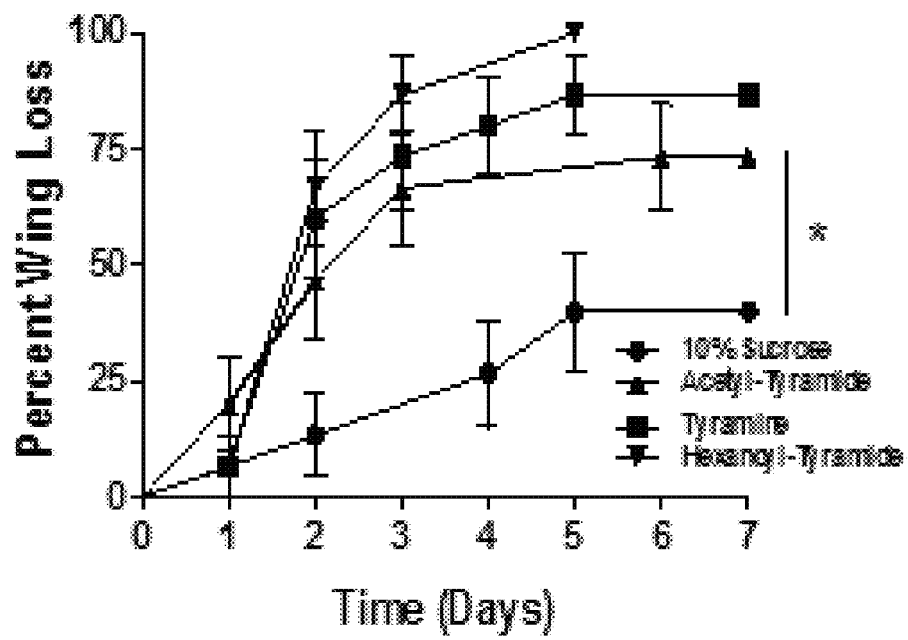
FIG. 11A-11B illustrate that (A) feeding tyramine and/or the tyramides to colony sub-units that contained immature female alates results in inappropriate wing loss, as well as ovariole development (data not shown), and (B) worker mortality, and likely wing muscle histolysis and queen pheromone production.
Figure 11B:
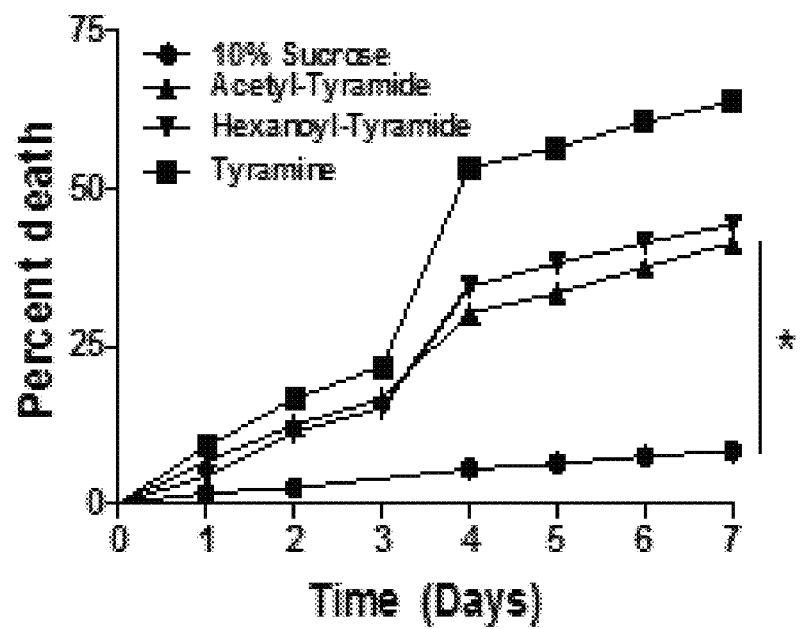

In this example, whether feeding tyramine and/or the tyramides to colony sub-units that contained female alates would result in inappropriate wing loss, as well as ovariole development. Wing muscle histolysis, and queen pheromone production normally accompanies wing loss (see Vargo, E. L. (1998), Primer pheromones in ants, pp. 293-313. In R. K. Vander Meer, M. D. Breed, K. E. Espelie and M. L. Winston (eds.), Pheromone communication in social insects ants, wasps, bees, and termites. Westview Press, Boulder, Colo.). Queenless colonies with brood, workers, and low weight (immature) female alates (n=5, 3 replicates per treatment and control) were setup. The units were fed tyramine and tyramides in 10% sucrose continuously for 7 days. The results shown in FIG. 11A surprisingly showed wing loss in all treatments significantly greater than control. The data supports and confirms that workers are feeding the treatments to the female alates, which in turn stimulates wing loss in the alates. FIG. 11B is from the same experiment confirming the worker mortality effects of the tyramine and tyramide treatments.

Example 12

Figure 12A:
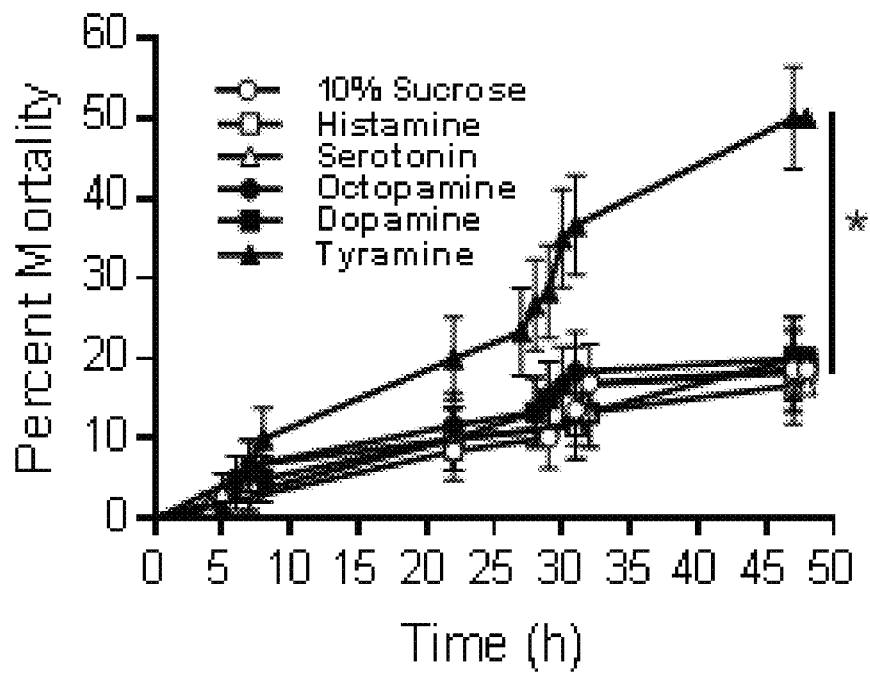
FIG. 12A-12B shows mortality results for five biogenic amines fed to fire ant workers.
Figure 12B:
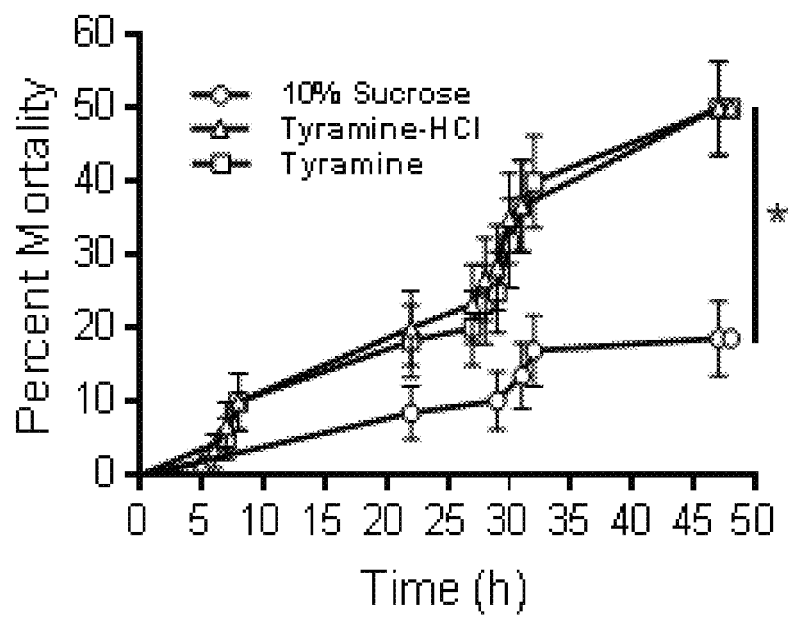

Tyramine is one of five biogenic amines that may be found in insects (e.g., dopamine, histamine, octopamine, serotonin, and tyramine). The experiment in this example tests whether fire ant worker mortality effects observed with tyramine may be a general result of the ants ingesting greater than normal amounts of a biogenic amine. To test this hypothesis groups of 20 fire ant worker ants were starved for 24 hours and fed a 1% (w/v) biogenic amine in 10% sucrose solution. Treatments and sucrose were presented to the worker ants as a 25 microliter droplet on a 2 $cm^2$ piece of silicon treated filter paper. Each treatment and control were performed in triplicate for a total of 60 worker ants per treatment and control. Mortality was monitored for the first 7-8 h after introduction of the sucrose solutions, then at 24 h. The feeding/monitoring sequence was repeated for another 24 h period for a total of 48 h. The results are shown in FIG. 12A-12B in the form of Kaplan-Meier mortality curves. FIG. 12A shows results for five biogenic amines at 1% as their HCl salts. It is quite surprising and clear that tyramine HCl resulted in statistically greater mortality than the control and the other 4 biogenic amines. Thus, the effect of tyramine is surprisingly not a general biogenic amine effect and is specific to tyramine. FIG. 12B illustrates that results for the tyramine HCl and the tyramine free base are not significantly different.

Example 13

Figure 13:
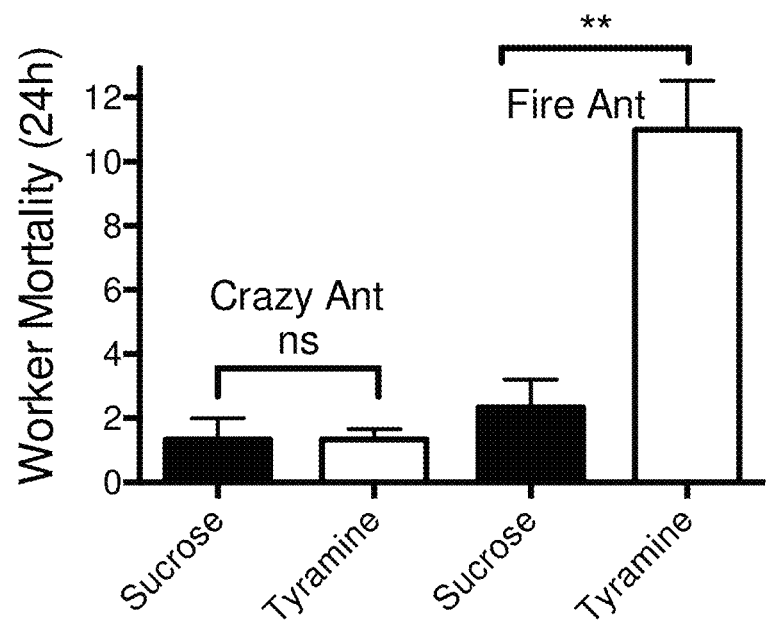
FIG. 13 shows that tyramine has specificity for certain ant species and does not cause worker mortality in all ant species.

To evaluate the effect of tyramine on another pest ant species triplicate groups of 20 Tawny crazy ant (*Nylanderia fulva*) workers and triplicate groups of 20 fire ant workers were setup. Corresponding controls for both pest ant species were workers fed 10% sucrose solution. The treatment was 1% tyramine in 10% sucrose (weight-to-volume). The control and treatments were presented to the worker ants as droplets on phase separation filter paper. Consumption of the droplets was readily observed. Mortality was monitored for each of the first 10 hours and then at 24 hours. The results are shown as mean±standard error of accumulated mortality for controls and treatments at 24 h in FIG. 13. Surprisingly, the tawny crazy did not have significant mortality compared to its sucrose control; however, as observed previously, fire ant workers had significant mortality compared to its sucrose control. These unexpected results illustrate that the toxicity effects of tyramine on fire ants are not automatically extended to other ant species.

Example 14

This Example relates to FIG. 14 to 23. Unless otherwise noted, the experiments were conducted using the following protocols.

Source of Fire Ant Workers.

*Solenopsis invicta* colony fragments were collected by excavation from field populations near Gainesville, Fla., known to have the monogyne (single queen) social form, based on aggression bioassays and genetic analysis (see e.g., Morel L, et al., Comparison of nestmate recognition between monogyne and polygyne populations of *Solenopsis invicta* (Hymenoptera: Formicidae). Annals of the Entomological Society of America. 1990; 83(3):642-7); Valles S M & Porter S D. Identification of polygyne and monogyne fire ant colonies (*Solenopsis invicta*) by Multiplex PCR of Gp-9 alleles. [poster paper]. p. 116, In: L. Greenberg & C. Lerner [ed.], Proceedings of the 2003 Red Imported Fire Ant Conference, Mar. 30-Apr. 1, 2003, Palm Springs, Calif., 145 p.; 2003). For these experiments, colony fragments containing workers, brood, sometimes male and female sexuals were quickly shoveled into a 19 L bucket with its upper inside surface dusted with talcum powder to prevent escapes. In the laboratory, colony life forms were removed from the soil by slowly flooding the containers as previously described (see e.g., Banks W A, et al., Techniques for collecting, rearing, and handling imported fire ants. USDA, SEA, AATS-S-21, 9 p.; 1981) and placed in colony trays. All colonies with or without a queen were provided crickets, water, and 10% sucrose solution and maintained in the laboratory under ambient conditions. These colonies tested negative for SINV-3 virus, which if present could confound interpretation of the results. Female sexuals were collected from fully functional queenright colonies (i.e., colonies containing queen, brood, workers, and sexuals).

Initial Feeding Experimental Procedure.

Preliminary experiments were conducted to probe the effects of test compounds on fire ant workers. Worker fire ants (n=20) were starved overnight and placed in 120 mL plastic cups with the upper inner surface coated with Fluon®. The ants in plastic cups were placed in a tray (50×40×12 cm) with its inner sides coated with Fluon. Three plastic containers (250 mL) were filled with water and placed in each experimental tray to keep the relative humidity high. A 2×2 cm piece of phase separation (hydrophobic) filter paper was placed in each cup containing worker ants. Treatments were dissolved in 10% sucrose solution at 1% (w/v). The control was 10% sucrose. Droplets (25 µl) of treatments or controls were deposited by syringe on the phase separation filter paper in each treatment and control.

The number of ants feeding at the droplet was recorded every 5 min for the first hour, then every hour for a total of 8 h. If the ants consumed the droplet within the 8 h of the experiment (about 4 to 5 hr), another 25 µl droplet was provided. Mortality was recorded each hour and at 21-24 h (total of 12 evaluations).

Test Tube Feeding Experimental Procedure.

Worker ants (250 mg, 300-320 individuals) were weighed and placed in plastic containers (16×4×10 cm) coated on the inside wall with Fluon. Each tray had a nest chamber composed of a glass test tube (15×1.5 cm) filled sequentially with 6 cm water, cotton plug, and 2 cm of Castone®. Treatments were dissolved in 10% sucrose solution at 1% or 0.1%, or 0.01% (w/v). The control was 10% sucrose. Twelve ml of treatments or controls were presented to the worker ant bioassay units in a 15 ml test tube, closed with a cotton plug. Worker ant mortality was recorded at every 24 h. One previously frozen and thawed cricket was provided after the first 24 h. The cricket was replaced every other day. In some experiments, low weight or high weight female alates (alate/workers combinations were from the same colony) were included in the experimental units along with the workers. In addition to monitoring worker mortality, alates were monitored for wing loss (dealation), ovariole development, and queen pheromone production. These physiological actions are normally observed directly after mating. Dead ants were counted and removed each day and pooled for each replicate. Dealates were also removed immediately and placed in separate nest chambers, described above. Dealates from a replicate were pooled in the same chamber. Test tubes containing treatment or control sucrose were refilled or replaced as needed during the course of experiment. Dealates were dissected for measurement of ovariole development and their poison sac was extracted for olfactometer evaluation within 24 h of wing loss.

Figure 14:
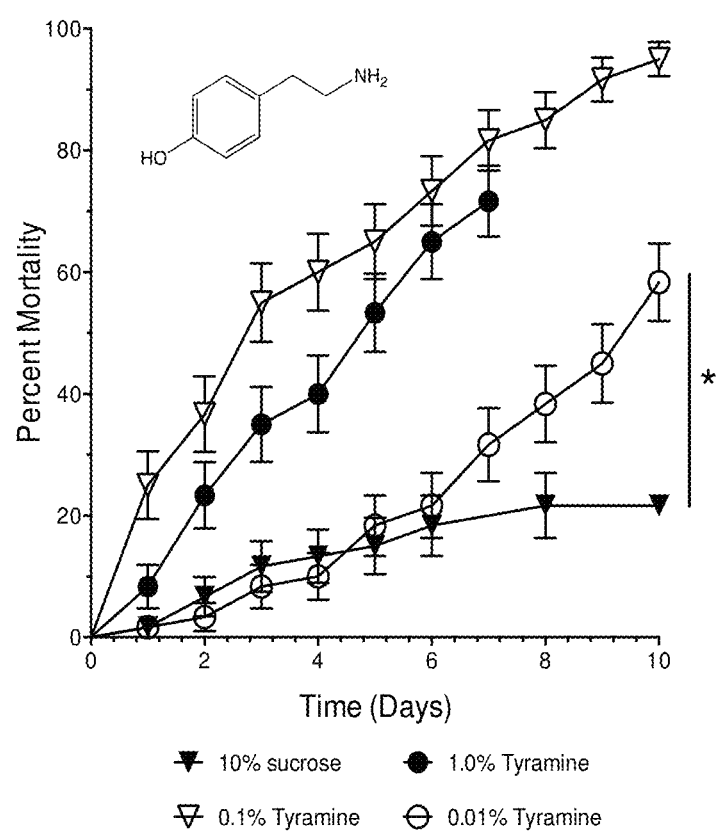
FIG. 14 shows fire ant worker mortality was significantly different from a control when fed tyramine at a 100-fold range of concentrations.

FIG. 14 shows fire ant worker mortality with 1.0, 0.1, and 0.01% concentrations of tyramine (free base) in 10% sucrose are all significantly different from the 10% sucrose control. The 1.0 and 0.1% tyramine are not significantly different, but they both are different from the 0.01% tyramine treatment. Significant mortality over 100-fold dilution, as seen here, is a key characteristic of an effective fire ant bait insecticide. The 1.0 and 0.1% are not significantly different (p=0.08), however, both are different from the 0.01% solution (p<0.0001).

Figure 15:
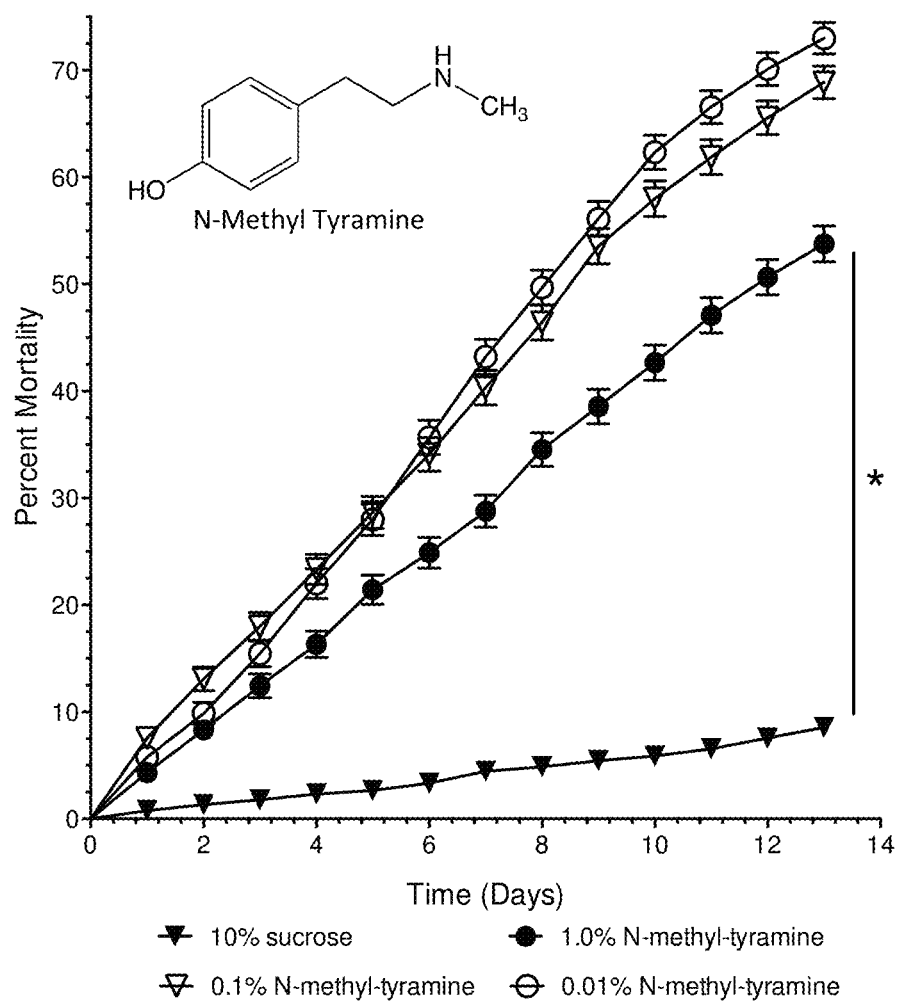
FIG. 15 shows fire ant worker mortality was significantly different from a control when fed N-methyl-tyramine over a 100-fold range of concentrations.

FIG. 15 shows fire ant worker mortality with 1.0, 0.1, and 0.01% concentrations of the tyramine derivative, N-methyl-tyramine (free base) in 10% sucrose. All concentrations are significantly different from the 10% sucrose control. Significant fire ant worker mortality for 1.0, 0.1, and 0.01% concentrations of N-methyl-tyramine (100-fold dilution) is a key characteristic of an effective fire ant bait insecticide. Interestingly, the two lower concentrations (0.1 and 0.01%) show significantly higher mortality than the 1.0% concentration. It is possible that the 1.0% N-methyl tyramine is not as palatable as the lower concentrations. The 0.1 and 0.01 concentrations are not significantly different (p=0.11).

Figure 16:
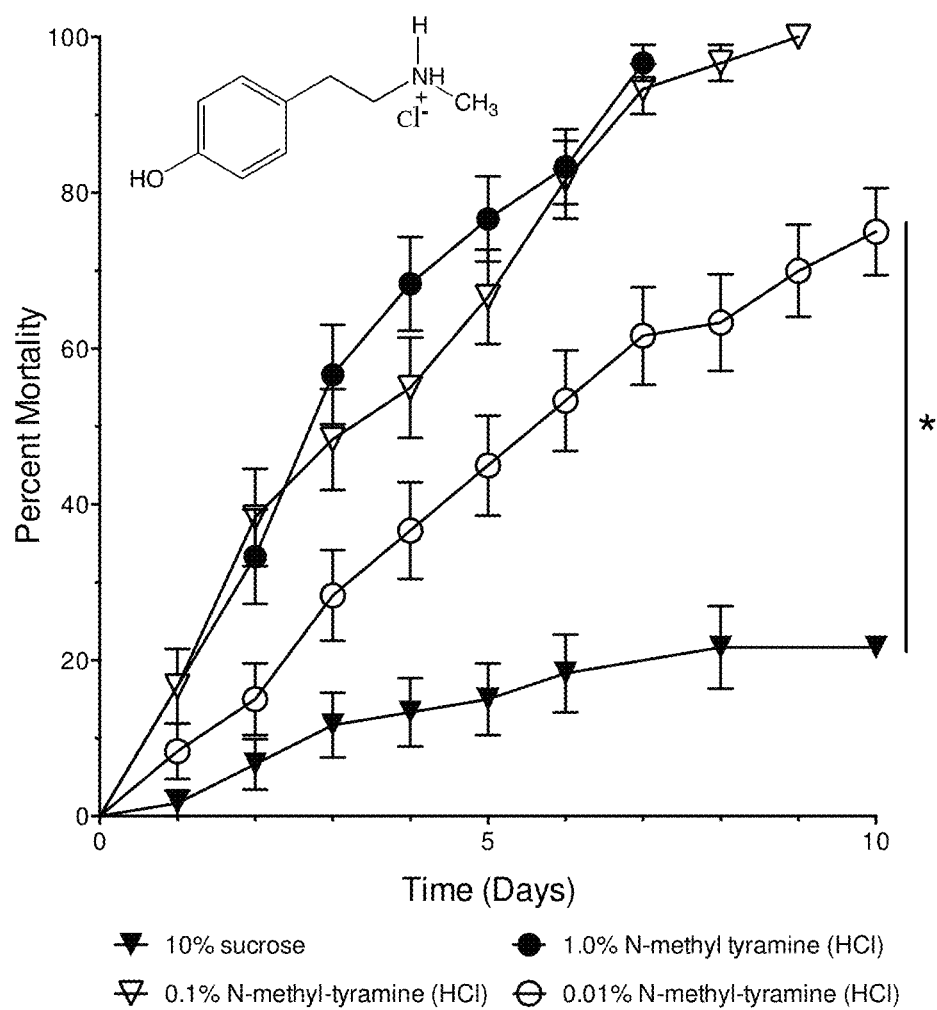
FIG. 16 shows fire ant worker mortality was significantly different from a control when fed a 100-fold range of concentrations of N-methyl-tyramine (HCl).
Figure 17:
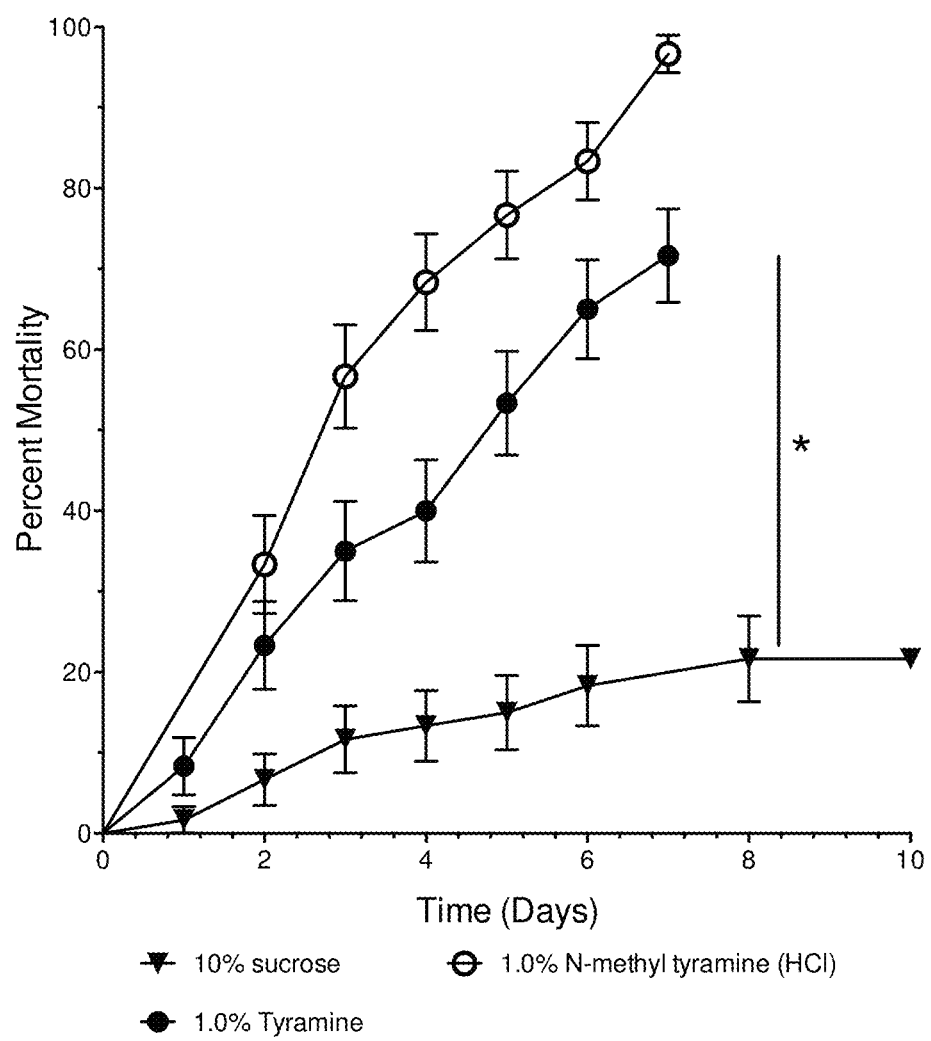
FIG. 17 shows a comparison of the effects of like concentrations of tyramine and N-methyl tyramine (HCl) versus a control, after being fed to fire ant workers.
Figure 18:
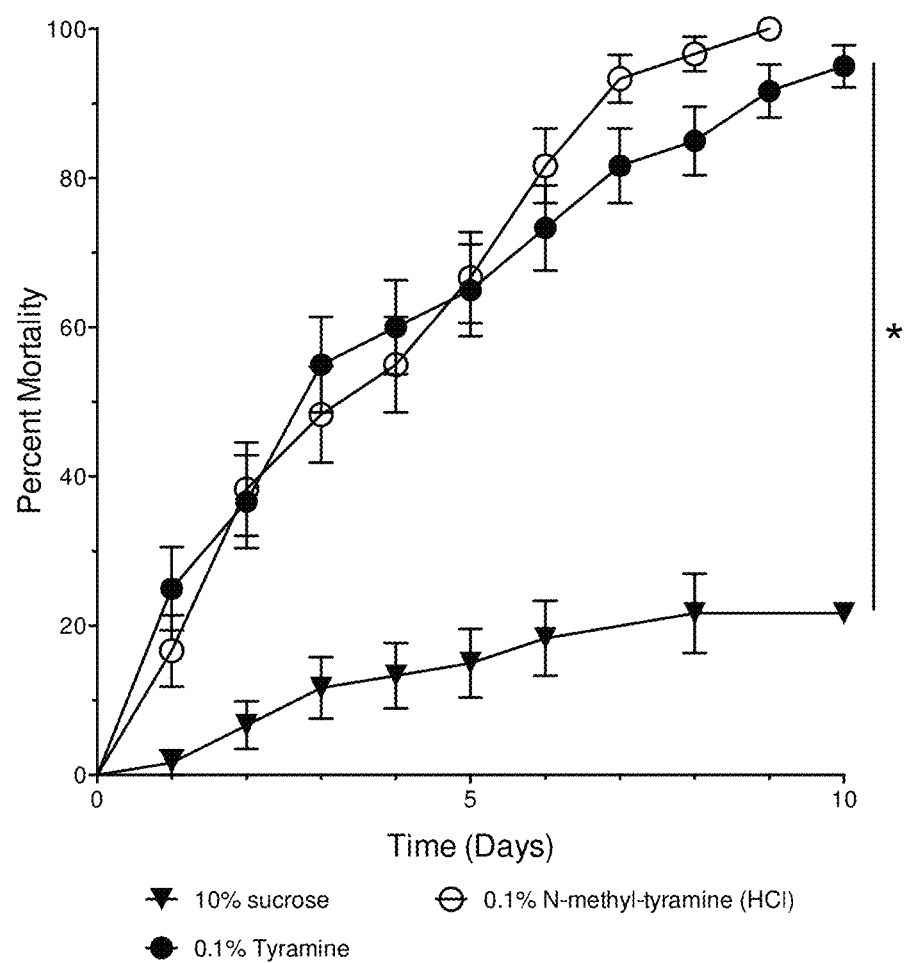
FIG. 18 shows a comparison of the effects of like concentrations of tyramine and N-methyl tyramine (HCl) versus a control, after being fed to fire ant workers.
Figure 19:
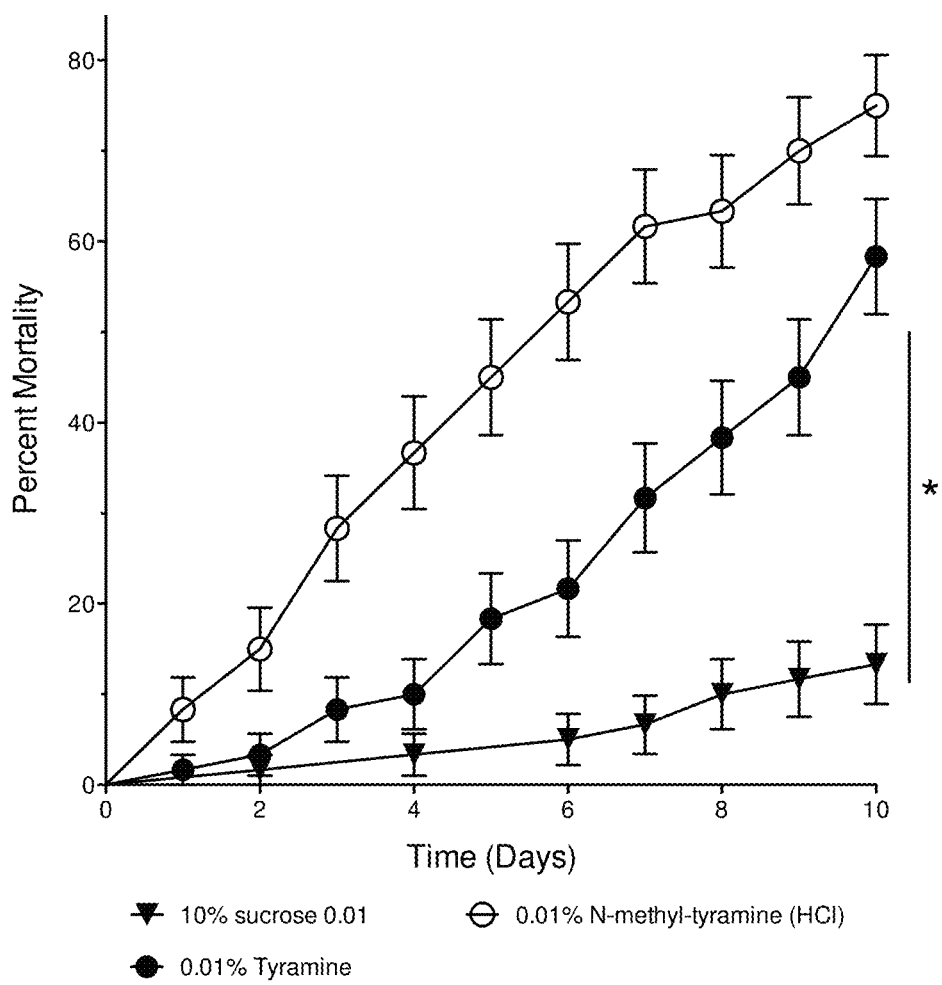
FIG. 19 shows a comparison of the effects of like concentrations of tyramine and N-methyl tyramine (HCl) versus a control, after being fed to fire ant workers.

FIG. 16 shows fire ant worker mortality is shown for 1.0, 0.1, and 0.01% concentrations of the tyramine derivative N-methyl-tyramine (HCl). All three concentrations are significantly different from the sucrose control. These results are important because the cost of the HCl salt is less than the free base, making it potentially a more cost-effective option for commercialization. Also, significant mortality over 100-fold dilution is a key characteristic of an effective fire ant bait insecticide. The 1.0% and 0.1% concentrations are significantly different from the 0.01 concentration (p<0.0001). The 1% and 0.1% are not significantly different (p=0.63). The N-methyl tyramine HCl appears to be quicker acting compared to the N-methyl tyramine free-base. FIGS. 17, 18, and 19 use N-methyl tyramine HCl for comparisons with tyramine at the same concentrations, due to the advantages noted above. The results show greater mortality for the N-methyl derivative than the tyramine at the same concentrations (see details below). In contrast, fire ant worker feeding experiments with 1% N,N-dimethyl-tyramine showed no difference in mortality (results not shown) from the 10% sucrose control (P=0.97). Therefore, the addition of another methyl group on the nitrogen negated the worker mortality activity observed with tyramine and N-methyl-tyramine. This suggests that the added steric hindrance of a second methyl group prevents its interaction with one or more critical receptors.

FIG. 17 shows a comparison of the effects of 1.0% concentrations of tyramine and 1.0% N-methyl tyramine (HCl) versus the 10% sucrose control. The 1.0% N-methyl tyramine (HCl) shows significantly faster worker mortality than the 1.0% tyramine (p<0.001). Mortality results for both treatments are significantly different from the sucrose control.

FIG. 18 shows a comparison of the effects of 0.1% concentrations of tyramine and N-methyl tyramine (HCl) versus the 10% sucrose control. Mortality results for both treatments are significantly different from the sucrose control. Fire ant worker mortality results for 0.1% N-methyl tyramine (HCl) are not significantly faster than the 0.1% tyramine (p=0.22).

FIG. 19 shows a comparison between 0.01% concentrations of tyramine and 0.01% N-methyl tyramine (HCl) versus the 10% sucrose control. Mortality results for both treatments are significantly different from the sucrose control. Fire ant worker mortality for 0.01% N-methyl tyramine (HCl) is significantly faster than the 0.01% tyramine (p<0.01). This result further supports the advantage of the N-methyl tyramine HCl over the free base.

Figure 20:
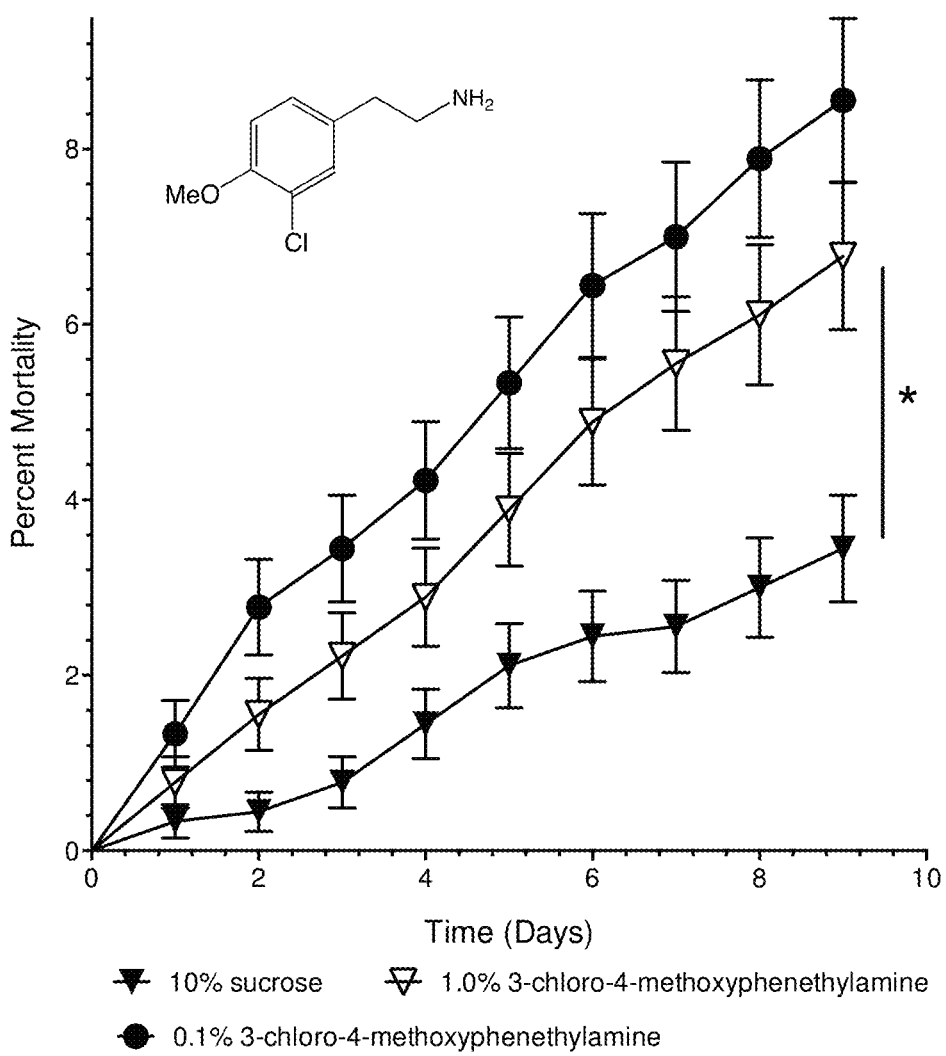
FIG. 20 shows fire ant mortality results for two concentrations of 3-chloro-4-methoxyphenethylamine versus a control, after being fed to fire ant workers.

FIG. 20 shows fire ant mortality results for two concentrations (1.0 and 0.1% in 10% sucrose) of 3-chloro-4-methoxyphenethylamine. Both treatment concentrations were significantly different from the 10% sucrose control. Mortality for the 0.1% concentration was not significantly greater than that for the 1.0% concentration (p=0.15). While the results were significant, the mortality (about 8%) was not high enough to warrant further testing.

Figure 21:
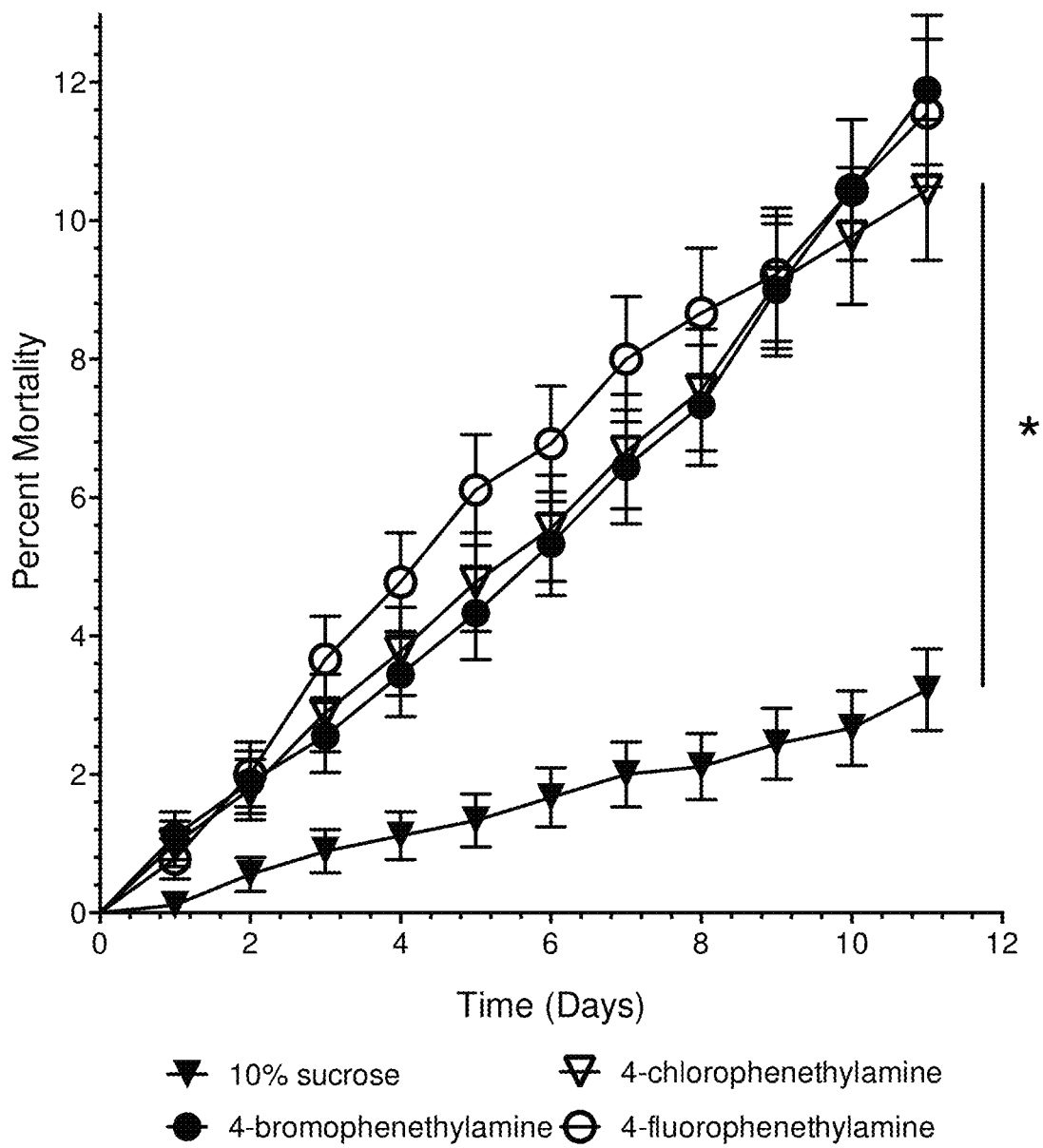
FIG. 21 shows worker mortality results for tyramine derivatives when the 4-hydroxyl group is replaced by a halogen: 4-chloro-, 4-bromo-, and 4-flurophenethylamine, after being fed to fire ant workers.

FIG. 21 shows worker mortality results for tyramine derivatives when the 4-hydroxyl group is replaced by a halogen. Significant, but low, worker mortality occurs for 4-chloro-, 4-bromo-, and 4-flurophenethylamine. All concentrations were at 1.0% in 10% sucrose solution. There are no differences between the three halogen derivatives (p=0.62). In contrast, fire ant worker mortality was measured (data not shown) for 1% concentrations of the three possible 2- or 3- or 4-methoxy-phenethylamine (tyramine) derivatives. No difference in mortality (p=0.12) was observed when compared to 10% sucrose control (data not shown).

Figure 22:
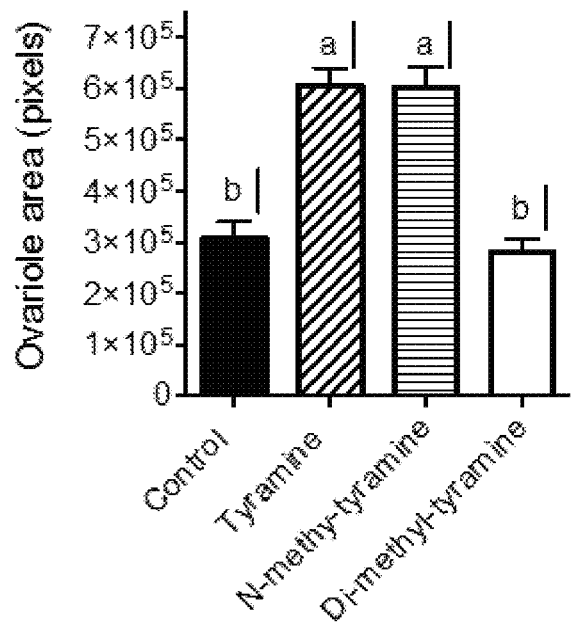
FIG. 22 shows a comparison of planar ovariole area (pixels) measurements of treatment and control sub-colonies composed of female sexuals with workers, but no queen, after being fed the indicated treatments/control, and after the female sexuals lost their wings.
Figure 23:
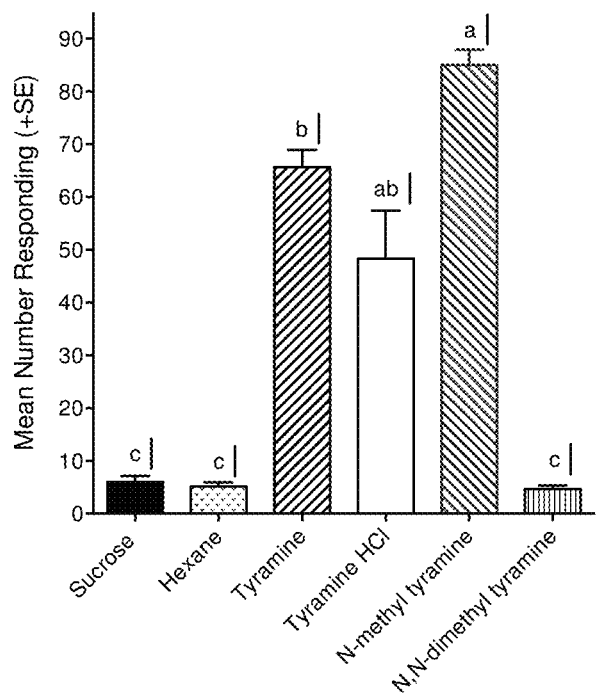
FIG. 23 shows results from a bioassay that measured attraction of workers to female sexual poison gland extracts, after the female sexuals lost their wings.

FIGS. 22 and 23 show two physiological events: (i) ovariole development and (ii) production of a worker attractant pheromone. Both events occur when female sexuals (alates) are removed from their mother colony and out of the influence of the colony queen. Under these conditions female alates will lose their wings and start ovariole development and pheromone production. The alates in treatments and controls were monitored once every 24 h for loss of wings (dealation). The ovarioles and poison sacs from dealates were immediately dissected. The poison sacs were immersed in hexane (30 μl) and placed in a vial and kept frozen until used in the queen pheromone bioassay (see below). Digital pictures of the ovarioles were taken directly after dissection for subsequent quantification by measuring the planar area of each of the two ovariole clusters (Leica Application Suite 4.4.02, Leica Microsystem (Switzerland), with an interactive measurement module). The level of worker attraction to poison sac extracts from dealates was quantified using a procedure modified from Lofgren, et al. 1983 (Annals ESA. 1983; 76:44-50).

FIG. 22 shows a comparison of planar ovariole area (pixels) measurements of treatment and control sub-colonies (N=15/treatment or control) composed of alates with workers, but no queen, after being fed the indicated treatments/control. Control was 10% sucrose and the treatments were 1% tyramine or 1% N-methyl-tyramine, or 1% Di-methyl-tyramine. Bars with the same letter above them are not significantly different (p>0.05), whereas they are significantly different (p<0.05) if the letters are different. Therefore, results for tyramine and N-Methyl tyramine are not different from each other, but are different from dimethyl tyramine and the sucrose control.

FIG. 23 shows results from a bioassay that measured attraction of workers to female sexual poison gland extracts. Bars with the same letter above them are not significantly different (p>0.05), whereas they are significantly different (p<0.05) if the letters are different. Therefore, poison sac extracts from N-methyl tyramine treatments induced significantly greater worker attraction than poison sac extracts from tyramine treatments; however, worker attraction to poison sac extracts from tyramine, tyramine HCl, and N-methyl tyramine treatments were significantly different from those from the N,N-dimethyl tyramine treatment and the sucrose and hexane controls. The tyramine HCl was not different from tyramine or N-methyl tyramine because of its greater replicate variance. N-methyl tyramine showed low variance and the highest worker response.

Example 15

Figure 24A:
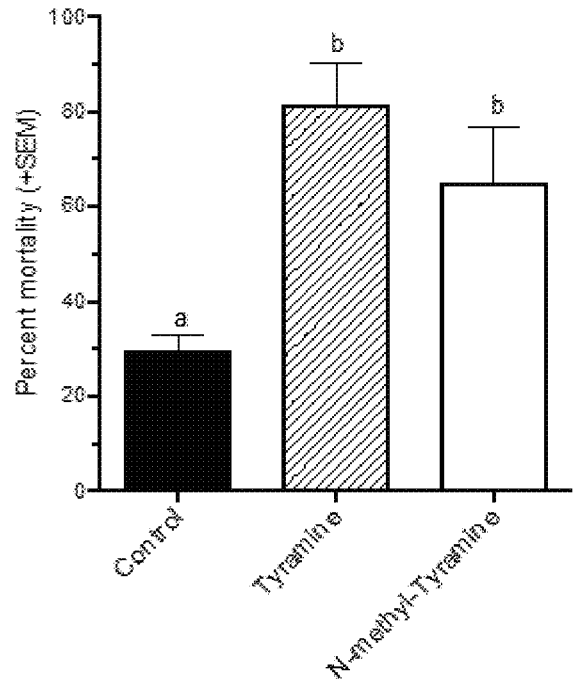
FIG. 24A-24B show mortality was significantly different from a control when mongyne queenright colonies were fed tyramine or N-methyl-tyramine.
Figure 24B:
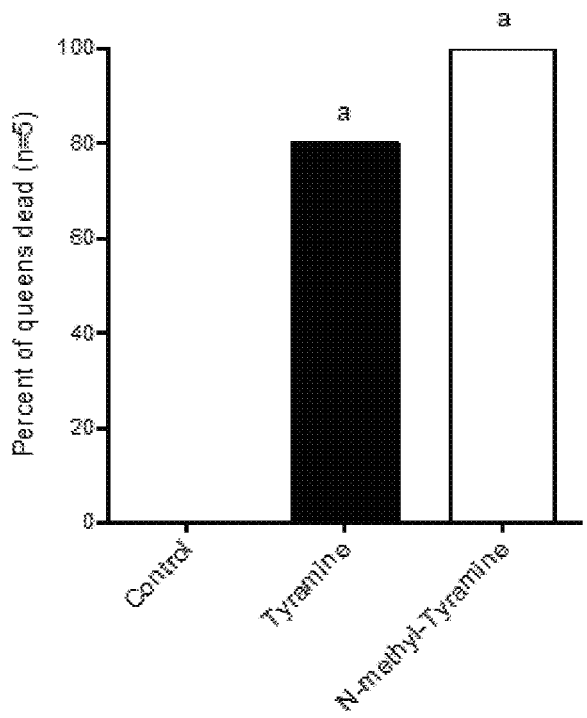

FIGS. 24A and 24B show results for the sucrose (10%) control and two treatments, tyramine (1%) and N-methyl-tyramine (1%), both dissolved in 10% sucrose. The control and test colonies were monogyne queenright colonies, containing a single queen, brood and workers started in the laboratory from newly mated queens collected in the field. The mean number of workers per colony was 8,400±400. FIG. 24A shows the % worker mortality at the end of the experiment (27 d). FIG. 24B shows queen mortality results at the end of the experiment. Bars with the same letter above them are not significantly different (p>0.05), whereas they are significantly different (p<0.05) if the letters are different. Therefore, for both worker and queen mortality, the results for tyramine and N-methyl tyramine are not different from each other, but are significantly different from the corresponding controls. Previous experiments used queenless sub-colonies, rather than the queenright colonies in these experiments. The mortality effect on colony queens was unexpected, since worker fire ants are completely sterile and cannot reproduce even if the queen dies. Therefore, when the reproductive queen dies no more brood is produced and the colony is no longer functional—it is considered dead. For N-methyl tyramine all queen replicates (5) died; therefore, 100% of the colonies were considered dead. For tyramine one colony queen survived out of five. Therefore, 80% of the treated colonies were considered dead.

The results demonstrate the surprising and unexpected negative effect of tyramine and its derivatives on of fire ants. While the dosages used are significantly higher than naturally found within colonies, the highly deleterious effects on fire ant colonies when delivered at such dosage levels was surprising and unexpected. These compounds are not known to have deleterious effects on insects. The expectations of one skilled in the art would not include such predictions, particularly when coupled with known properties of the biogenic amines and the differences observed among the biogenic amines tested and the absence of effect on a different ant species.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments and characteristics described herein and/or incorporated herein. In addition the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 30%, preferably by as much as 20%, and more preferably by as much as 10% to a reference quantity, level, value, or amount.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims. Although any methods and materials similar or equivalent to those described herein can be used in the practice or testing of the present invention, the preferred methods and materials are herein described. Those skilled in the art may recognize other equivalents to the specific embodiments described herein which equivalents are intended to be encompassed by the claims attached hereto.

The claimed invention is:

1. A method of controlling a population of fire ants, the method comprising delivering a composition comprising an effective amount of tyramine to the population of fire ants, wherein the effective amount of tyramine delivered on a per fire ant worker basis is at least about fifty times greater than an average amount of naturally-occurring tyramine within fire ant workers in the population of fire ants, and wherein the effective amount of tyramine is sufficient to cause mortality within the population of fire ants.

2. The method of claim 1, wherein the composition further comprises a phagostimulant.

3. The method of claim 1, wherein the amount of tyramine delivered on the per fire ant worker basis is at least about one thousand times greater than the average amount of naturally-occurring tyramine within fire ant workers in the population of fire ants.

4. The method of claim 1, wherein the amount of tyramine delivered on the per fire ant worker basis is from about one thousand times to about ten thousand times greater than the average amount of naturally-occurring tyramine within fire ant workers in the population of fire ants.

5. The method of claim 1, wherein the composition comprises an aqueous solution of tyramine from about 0.01 wt % to about 1.0 wt %.

6. The method of claim 1, wherein the tyramine is present in a sufficient quantity such that it is delivered to the population of fire ants at least about 0.01 micrograms per fire ant in the population of fire ants.

7. The method of claim 1, wherein the composition comprising tyramine is in a form selected from the group consisting of: substantially pure, solid, liquid, aqueous solution, semi-solid, spay, powder, granule, tablet, gel, cream, lotion, and combinations thereof.

8. The method of claim 1, wherein the composition comprising tyramine further comprises a component selected from the group consisting of: liquid diluent, solid diluent, surfactant, additive, preservative, and combinations thereof.

9. The method of claim 1, wherein the composition comprising tyramine further comprises a component selected from the group consisting of: a phagostimulant, an ant-attractant component, an ant-toxic component, an ant-ingestible component, and combinations thereof.

10. The method of claim 1, wherein the population of fire ants comprises the species *Solenopsis invicta*.

11. The method of claim 1, wherein the effective amount of tyramine is from about 0.01 microgram to about 2.0 micrograms of the compound per fire ant in the population of fire ants.

12. The method of claim 1, wherein the composition further comprises one or more tyramine derivatives.

13. The method of claim 1, wherein the composition is in a form selected from the group consisting of: solid, liquid, semi-solid, spray, powder, granule, tablet, gel, cream, lotion, and combinations thereof.

14. The method of claim 1, wherein the composition further comprises a component selected from the group consisting of: an ant-attractant component, an ant-toxic component, an ant-ingestible component, and combinations thereof.

15. The method of claim 1, further comprising deploying the composition in a bait station.

* * * * *